(12) United States Patent
Behrens et al.

(10) Patent No.: US 9,018,166 B2
(45) Date of Patent: Apr. 28, 2015

(54) CONJUGATED FVIII VARIANTS

(75) Inventors: Carsten Behrens, København N (DK);
Jens Buchardt, Gentofte (DK); Magali Zundel, Dyssegaard (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/577,310

(22) PCT Filed: Feb. 7, 2011

(86) PCT No.: PCT/EP2011/051723
§ 371 (c)(1),
(2), (4) Date: Aug. 29, 2012

(87) PCT Pub. No.: WO2011/101267
PCT Pub. Date: Aug. 25, 2011

(65) Prior Publication Data
US 2012/0322738 A1 Dec. 20, 2012

Related U.S. Application Data

(60) Provisional application No. 61/305,608, filed on Feb. 18, 2010.

(30) Foreign Application Priority Data

Feb. 16, 2010 (EP) .................................... 10153718

(51) Int. Cl.
| | | |
|---|---|---|
| C07K 14/755 | (2006.01) | |
| A61P 7/04 | (2006.01) | |
| A61K 38/37 | (2006.01) | |
| A61K 47/48 | (2006.01) | |
| A61K 38/00 | (2006.01) | |

(52) U.S. Cl.
CPC .............. *C07K 14/755* (2013.01); *A61K 38/00* (2013.01); *A61K 47/48215* (2013.01); *A61K 47/48561* (2013.01)

(58) Field of Classification Search
CPC ............ A61K 38/00; A61K 47/48561; A61K 47/48215; C07K 14/755
USPC ....................................................... 514/14.1
See application file for complete search history.

(56) References Cited

U.S. PATENT DOCUMENTS

| | | | |
|---|---|---|---|
| 4,356,170 A | 10/1982 | Jennings et al. | |
| 5,932,462 A | 8/1999 | Harris et al. | |
| 6,759,216 B1 * | 7/2004 | Lollar | 435/69.6 |
| 7,157,277 B2 * | 1/2007 | DeFrees et al. | 435/351 |
| 2007/0105755 A1 * | 5/2007 | DeFrees et al. | 514/8 |
| 2009/0076237 A1 * | 3/2009 | Turecek et al. | 527/207 |

FOREIGN PATENT DOCUMENTS

| | | |
|---|---|---|
| WO | 03/031464 A2 | 4/2003 |
| WO | 03/062290 A1 | 7/2003 |
| WO | 2005/016974 A1 | 2/2005 |
| WO | 2006/053299 A2 | 5/2006 |
| WO | 2006/090119 A1 | 8/2006 |
| WO | 2006/103298 A2 | 10/2006 |
| WO | 2006/134148 A2 | 12/2006 |
| WO | 2007/087711 A1 | 8/2007 |
| WO | 2007/126808 A1 | 11/2007 |
| WO | 2008/011633 A2 | 1/2008 |
| WO | 2008/074032 A1 | 6/2008 |
| WO | 2008/151258 | 12/2008 |
| WO | 2008/151448 A1 | 12/2008 |
| WO | 2009/062100 A1 | 5/2009 |
| WO | 2009/089396 | 7/2009 |
| WO | 2009/108806 A1 | 9/2009 |
| WO | WO 2009108806 A1 * | 9/2009 |
| WO | 2010/014708 A2 | 2/2010 |
| WO | 2010/045568 A1 | 4/2010 |
| WO | 2010/102886 A1 | 9/2010 |

OTHER PUBLICATIONS

Haack, et al. Analysis of expression kinetics and activity of a new B-domain truncated and full-length FVIII protein in three different cell lines, Annals of Hematology 78:111-116, 1999).*

Harduin-Lepers, The human sialyltransferase family, Biochimie 83:727-737, 2001.*

Groner et al., Journal of Thrombosis and Haemostasis, "Abstracts From XXII ISTH Congress", 2009, vol. 7, No. SUPPL2, pp. 508-517.

Angata et al., Journal of Biological Chemistry, "ST8SIA II and ST8SIA IV Polysialyltransferases Exhibit Marked Differences in Utilizing Various Acceptors Containing Oligosialic Acid and Short Polysialic Acid", 2002, vol. 277, No. 39, pp. 36808-36817.

Bonora et al., Post-translational Modification of Protein Biopharmaceuticals, "Engineering in a PTM: Pegylation.", 2009, pp. 341-357.

"Cho, JW. et al., Proceedings of the National Academy of Sciences of the United Sta, ""Polysialic Acid Engineering: Synthesis of Polysialylated Neoglycosphingolipids by Using the Polysialyltransferase From Neuroinvasive *Escherichia coli* K1""", 1994, vol. 91, No. 24, pp. 11427-11431".

Eckhardt et al., Nature, "Molecular Characterization of Eukaryotic Polysialyltransferase-1", 1995, vol. 373, pp. 715-718.

"Fernandes et al., Biochimica et Biophysica Acta, ""Synthesis, Characterization and Properties of Sialylated Catalase Synthesis, Characterization and Properties of Sialylated Catalase """, 1996, vol. 1293, pp. 90-96".

Fontana et al., Advanced Drug Delivery Reviews, "Site-Specific Modification and Pegylation of Pharmaceutical Proteins Mediated by Transglutaminase", 2008, vol. 60, No. 1, pp. 13-28.

(Continued)

*Primary Examiner* — Julie Ha
*Assistant Examiner* — Li Ni Komatsu
(74) *Attorney, Agent, or Firm* — Nonna G. Akopyan; Reza Green; Richard W. Bork

(57) ABSTRACT

The present invention relates to conjugated Factor VIII variants. The present invention in particular relates to conjugated FVIII variants comprising different polymeric groups as well as use thereof.

9 Claims, 1 Drawing Sheet

(56) References Cited

OTHER PUBLICATIONS

Gilbert et al., Journal of Biological Chemistry, "The Genetic Bases for the Variation in The Lipo-Oligosaccharide of the Mucosal Pathogen, Campylobacter Jejuni", 2002, vol. 277, No. 1, pp. 327-337.

Glabe et al., Journal of Biological Chemistry, "Glycosylation of Ovalbumin Nascent Chains", 1980, vol. 255, No. 19, pp. 9236-9242.

Graham et al, Journal of General Virology, "Characteristics of a Human Cell Line Transformed by DNA From Human Adenovirus Type 5", 1977, vol. 36, pp. 59-72.

Gregoriadis et al., S.T.P. Pharma Sciences, "Polysialylated Proteins: An Approach to Improve Enzyme Stability and Half-Life in the Blood Circulation", 1999, vol. 9, No. 1, pp. 61-66.

Higuchi et al., Genomics, "Characterization of Mutations in the Factor VIII Gene by Direct Sequencing of Amplified Genomic DNA", 1990, vol. 6, No. 1, pp. 65-71.

Jain S et al, BBA—General Subjects, Elsevier Science Publishers, NL, "Polysialylated Insulin: Synthesis, Characterization and Biological Activity in Vivo", 2003, vol. 1622, No. 1, pp. 42-49.

Jennings and Lugowski, Journal of Immunology, "Immunochemistry of Groups A, B, and C Meningococcal Polysaccharide—Tetanus Toxoid Conjugates", 1981, vol. 127, No. 3, pp. 1011-1018.

Julenius, K. et al., Bioinformatics for Glycobiology and Glycomics:, "Prediction of Glycosylation Sites in Proteins", 2009, pp. 163-185.

Karin Julenius et al., Glycobiology, "Prediction, Conservation Analysis, and Structural Characterization of Mammalian Mucin-Type O-Glycosylation Sites", 2004, vol. 15, No. 2, pp. 153-164.

Kiely et al., Journal of Biological Chemistry, "Studies on the Attachement of Carbohydrate to Ovalbumin Nascent Chains in Hen Oviduct", 1976, vol. 251, No. 18, pp. 5490-5495.

Kojima et al., FEBS Letters, "A Developmentally Regulated Member of the Sialyltransferase Family (ST8SIA II, STX) is a Polysialic Acid Synthase", 1995, vol. 373, No. 2, pp. 119-122.

"Kunou M. et al., Biomacromolecules., ""Synthesis of Sulfated Colominic Acids and Their Nteraction With Fibroblast Growth Factors """, 2000, vol. 1, No. 3, pp. 451-458".

"Nakayama et al., Proceedings of the National Academy of Sciences of the USA, ""Expression Cloning of a Human Polysialyltransferase That Forms the Polysialylated Neural Cell Adhesion Molecule Present in Embryonic Brain""", 1995, vol. 92, No. 15, pp. 7031-7035".

P. J. Lenting et al., Haemophilia, "Factor VIII and Von Willebrand Factor—Too Sweet for Own Good", 2010, vol. 16, No. 5, pp. 194-199.

Saenko E L et al, Haemophilia, "Strategles Towards a Longer Acting Factor VIII", 2006, vol. 12, No. 3, pp. 42-51.

"Scheidegger et al., Journal of Biological Chemistry, ""A Human STX CDNA Confers Polysialic Acid Expression in Mammalian Cells """, 1995, vol. 270, No. 39, pp. 22685-22688".

Thim L, et al., Haemophilia, "Purification and Characterization of a New Recombinant Factor VIII(N8)", 2010, vol. 16, No. 2, pp. 349-359.

Urlaub G. et al, Somatic Cell and Molecular Genetics, "Effect of Gamma Rays at the Dihydrofolate Reductase Locus: Deletions and Inversions", 1986, vol. 12, No. 6, pp. 555-566.

Urlaub et al, Proceedings of the National Academy of Sciences of the USA, "Isolation of Chinese Hamster Cell Mutants Deficient in Dihydrofolate Reductase Activity", 1980, vol. 77, No. 7, pp. 4216-4220.

"Urlaub, Gail et al., Cell, ""Deletion of the Diploid Dihydrofolate Reductase Locus From Cultured Mammalian Cells""", 1983, vol. 33, No. 2, pp. 405-412".

Veronese et al, Journal of Bioactive and Compatible Polymers, "Branched and Linear Poly(Ethylene Glycol): Influence of the Polymer Structure on Enzymological, Pharmacokinetic, and Immunological Properties of Protein Conjugates", 1997, vol. 12, No. 3, pp. 196-207.

Veronese et al., Advanced Drug Delivery Reviews, "Introduction and Overview of Peptide and Protein Pegylation", 2002, vol. 54, pp. 453-456.

Waechter et al, Proceedings of the National Academy of Sciences of the USA, "Effect of Methylation on Expression of Microinjected Genes", 1982, vol. 79, pp. 1106-1110.

Willis et al., Glycobiology, "Characterization of the $\zeta$-2,8-Polysialyltransferase From *Neisseria meningitidis* With Synthetic Acceptors, and The Development of a Self-Priming Polysialyltransferase Fusion Enzyme", 2008, vol. 18, No. 2, pp. 177-186.

* cited by examiner

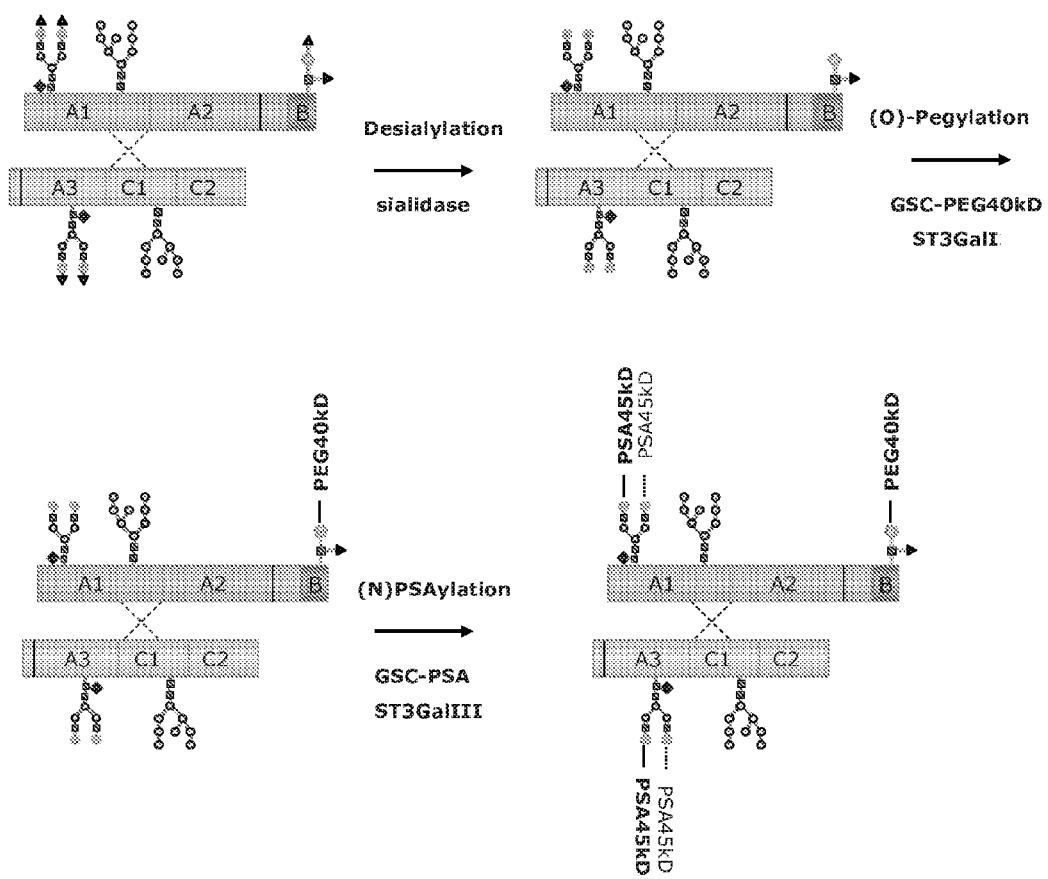

CONJUGATED FVIII VARIANTS

CROSS-REFERENCE TO RELATED APPLICATIONS

This application is a 35 U.S.C. §371 national stage application of International Patent Application PCT/EP2011/051723 (published as WO 2011/101267 A1), filed Feb. 7, 2011, which claimed priority of European Patent Application 10153718.1, filed Feb. 16, 2010; this application further claims priority under 35 U.S.C. §119 of U.S. Provisional Application 61/305,608, filed Feb. 18, 2010.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Aug. 1, 2012. The Sequence Listing is made up of 21 kilobytes, and the information contained in the attached "SEQUENCE LISTING" is identical to the information in the specification as originally filed. No new matter is added.

BACKGROUND

Haemophilia A is an inherited bleeding disorder caused by deficiency or dysfunction of coagulation factor VIII (FVIII) activity. The clinical manifestation is not on primary haemostasis—formation of the blood clot occurs normally—but the clot is unstable due to a lack of secondary thrombin formation.

Haemophilia A is currently treated by intravenously injection of coagulation factor FVIII which is either isolated from blood or produced recombinantly. Treatment can be either on-demand or prophylactic. Recent published data support that prophylaxis has significant advantages over on-demand treatment. These include reduction in bleeding frequency and lower risk of developing haemophilic arthropathy, both resulting in a better quality of life for the patients. However, while prophylaxis enables a virtually symptom-free life for the patients, it requires frequent injections in a peripheral vein, typically three times a week, which is known to be painful, difficult, and time consuming. In addition, repeated venipuncture is not always possible in young children. Consequently, a product supporting less frequent administration and/or administration would to a greater extent enable regular prophylactic treatment.

It has long been known that coupling of polymers like for example polyethyleneglycol (PEGs) or polysialic acids (PSAs) to a protein leads to increased circulation time, increased resistance towards proteases and reduced immunogenicity. There is, however, still a need in the art for FVIII variants having a prolonged circulatory half life.

SUMMARY

The present invention relates to FVIII variant conjugated with at least one PEG polymer and at least one polysaccharide as well as use thereof. It is shown herein that such heteroconjugated FVIII variants have an improved increase in circulatory half life over FVIII variants conjugated with e.g., two PEG molecules or two polysaccharide molecules.

BRIEF DESCRIPTION OF DRAWINGS

FIG. 1 shows an example of synthesis of a FVIII variant according to the present invention.

DESCRIPTION

Definitions

Factor VIII Molecules:

FVIII/Factor VIII is a large, complex glycoprotein that primarily is produced by hepatocytes. Human FVIII consists of 2351 amino acids, including signal peptide, and contains several distinct domains, as defined by homology. There are three A-domains, a unique B-domain, and two C-domains. The domain order can be listed as $NH_2$-A1-A2-B-A3-C1-C2-COOH. FVIII circulates in plasma as two chains, separated at the B-A3 border. The chains are connected by bivalent metal ion-bindings. The A1-A2-B chain is termed the heavy chain (HC) while the A3-C1-C2 is termed the light chain (LC).

FVIII circulates associated with von Willebrand Factor (vWF). vWF is a large multimeric glycoprotein that serves as a carrier for FVIII and is required for normal platelet adhesion to components of the vessel wall. The plasma-half life of FVIII in complex with VWF is approximately 12 hours.

"Native FVIII" is the full length human FVIII molecule as shown in SEQ ID NO:1 (amino acid 1-2332). The B-domain is spanning amino acids 741-1648 in SEQ ID NO:1.

```
SEQ ID NO 1:
ATRRYYLGAVELSWDYMQSDLGELPVDARFPPRVPKSFPFNTSVVYKK

TLFVEFTDHLFNIAKPRPPWMGLLGPTIQAEVYDTVVITLKNMASHPV

SLHAVGVSYWKASEGAEYDDQTSQREKEDDKVFPGGSHTYVWQVLKEN

GPMASDPLCLTYSYLSHVDLVKDLNSGLIGALLVCREGSLAKEKTQTL

HKFILLFAVFDEGKSWHSETKNSLMQDRDAASARAWPKMHTVNGYVNR

SLPGLIGCHRKSVYWHVIGMGTTPEVHSIFLEGHTFLVRNHRQASLEI

SPITFLTAQTLLMDLGQFLLFCHISSHQHDGMEAYVKVDSCPEEPQLR

MKNNEEAEDYDDDLTDSEMDVVRFDDDNSPSFIQIRSVAKKHPKTWVH

YIAAEEEDWDYAPLVLAPDDRSYKSQYLNNGPQRIGRKYKKVRFMAYT

DETFKTREAIQHESGILGPLLYGEVGDTLLIIFKNQASRPYNIYPHGI

TDVRPLYSRRLPKGVKHLKDFPILPGEIFKYKWTVTVEDGPTKSDPRC

LTRYYSSFVNMERDLASGLIGPLLICYKESVDQRGNQIMSDKRNVILF

SVFDENRSWYLTENIQRFLPNPAGVQLEDPEFQASNIMHSINGYVFDS

LQLSVCLHEVAYWYILSIGAQTDFLSVFFSGYTFKHKMVYEDTLTLFP

FSGETVFMSMENPGLWILGCHNSDFRNRGMTALLKVSSCDKNTGDYYE

DSYEDISAYLLSKNNAIEPRSFSQNSRHPSTRQKQFNATTIPENDIEK

TDPWFAHRTPMPKIQNVSSSDLLMLLRQSPTPHGLSLSDLQEAKYETF

SDDPSPGAIDSNNSLSEMTHFRPQLHHSGDMVFTPESGLQLRLNEKLG

TTAATELKKLDFKVSSTSNNLISTIPSDNLAAGTDNTSSLGPPSMPVH

YDSQLDTTLFGKKSSPLTESGGPLSLSEENNDSKLLESGLMNSQESSW

GKNVSSTESGRLFKGKRAHGPALLTKDNALFKVSISLLKTNKTSNNSA

TNRKTHIDGPSLLIENSPSVWQNILESDTEFKKVTPLIHDRMLMDKNA

TALRLNHMSNKTTSSKNMEMVQQKKEGPIPPDAQNPDMSFFKMLFLPE

SARWIQRTHGKNSLNSGQGPSPKQLVSLGPEKSVEGQNFLSEKNKVWG

KGEFTKDVGLKEMVFPSSRNLFLTNLDNLHENNTHNQEKKIQEEIEKK
```

-continued
```
ETLIQENVVLPQIHTVTGTKNFMKNLFLLSTRQNVEGSYDGAYAPVLQ

DFRSLNDSTNRTKKHTAHFSKKGEEENLEGLGNQTKQIVEKYACTTRI

SPNTSQQNFVTQRSKRALKQFRLPLEETELEKRIIVDDTSTQWSKNMK

HLTPSTLTQIDYNEKEKGAITQSPLSDCLTRSHSIPQANRSPLPIAKV

SSFPSIRPIYLTRVLFQDNSSHLPAASYRKKDSGVQESSHFLQGAKKN

NLSLAILTLEMTGDQREVGSLGTSATNSVTYKKVENTVLPKPDLPKTS

GKVELLPKVHIYQKDLFPTETSNGSPGHLDLVEGSLLQGTEGAIKWNE

ANRPGKVPFLRVATESSAKTPSKLLDPLAWDNHYGTQIPKEEWKSQEK

SPEKTAFKKKDTILSLNACESNHAIAAINEGQNKPEIEVTWAKQGRTE

RLCSQNPPVLKRHQREITRTTLQSDQEEIDYDDTISVEMKKEDFDIYD

EDENQSPRSFQKKTRHYFIAAVERLWDYGMSSSPHVLRNRAQSGSVPQ

FKKVVFQEFTDGSFTQPLYRGELNEHLGLLGPYIRAEVEDNIMVTFRN

QASRPYSFYSSLISYEEDQRQGAEPRKNFVKPNETKTYFWKVQHHMAP

TKDEFDCKAWAYFSDVDLEKDVHSGLIGPLLVCHTNTLNPAHGRQVTV

QEFALFFTIFDETKSVVYFTENMERNCRAPCNIQMEDPTFKENYRFHA

INGYIMDTLPGLVMAQDQRIRWYLLSMGSNENIHSIHFSGHVFTVRKK

EEYKMALYNLYPGVFETVEMLPSKAGIWRVECLIGEHLHAGMSTLFLV

YSNKCQTPLGMASGHIRDFQITASGQYGQWAPKLARLHYSGSINAWST

KEPFSWIKVDLLAPMIIHGIKTQGARQKFSSLYISQFIIMYSLDGKKW

QTYRGNSTGTLMVFFGNVDSSGIKHNIFNPPIIARYIRLHPTHYSIRS

TLRMELMGCDLNSCSMPLGMESKAISDAQITASSYFTNMFATWSPSKA

RLHLQGRSNAWRPQVNNPKEWLQVDFQKTMKVTGVTTQGVKSLLTSMY

VKEFLISSSQDGHQWTLFFQNGKVKVFQGNQDSFTPVVNSLDPPLLTR

YLRIHPQSWVHQIALRMEVLGCEAQDLY
```

"FVIII variants" according to the present invention may be FVIII derived from blood plasma and/or recombinant FVIII. FVIII variants according to the invention may be e.g., B-domain truncated FVIII molecules wherein e.g. the remaining domains correspond closely to the sequence as set forth in amino acid no 1-740 and 1649-2332 in SEQ ID NO:1. B domain truncated FVIII variants according to the invention may differ slightly from the sequence set forth in SEQ ID NO:1, meaning that the remaining domains (i.e., the three A-domains and the two C-domains) may differ slightly e.g. 1, 2, 3, 4, 5, 6, 7, 8, 9, or 10 amino acids, alternatively may differ about 1%, 2%, 3%, 4% or 5% from the amino acid sequence as set forth in SEQ ID NO:1 (amino acids 1-740 and 1649-2332) due to the fact that mutations can be introduced in order to e.g., reduce vWF binding capacity. Furthermore, it is plausible that amino acid modifications (substitutions, deletions, etc.) are introduced other places in the molecule in order to modify the binding capacity of Factor VIII with various other components such as e.g., LRP, various receptors, other coagulation factors, cell surfaces, introduction and/or abolishment of glycosylation sites, etc. FVIII variants according to the present invention have FVIII activity, meaning the ability to function in the coagulation cascade in a manner functionally similar or equivalent to FVIII, induce the formation of FXa via interaction with FIXa on an activated platelet, and support the formation of a blood clot. The activity can be assessed in vitro by techniques well known in the art such as e.g. chromogenic assay, clot analysis, endogenous thrombin potential analysis, etc. FVIII variants according to the invention have FVIII activity being at least about 10%, at least 20%, at least 30%, at least 40%, at least 50%, at least 60%, at least 70%, at least 80%, at least 90%, and 100% or even more than 100% of that of native human FVIII.

B-Domain:

The B-domain in Factor VIII spans amino acids 741-1648 in SEQ ID NO:1. The B-domain is cleaved at several different sites, generating large heterogeneity in circulating plasma FVIII molecules. The exact function of the heavily glycosylated B-domain is unknown. What is known is that the domain is dispensable for FVIII activity in the coagulation cascade. This apparent lack of function is supported by the fact that B-domain deleted/truncated FVIII appears to have in vivo properties identical to those seen for full length native FVIII. That being said there are indications that the B-domain may reduce the association with the cell membrane, at least under serum free conditions.

B Domain Truncated/Deleted Factor VIII Molecule:

Endogenous full length FVIII is synthesized as a single-chain precursor molecule. Prior to secretion, the precursor is cleaved into the heavy chain and the light chain. Recombinant B-domain deleted FVIII can be produced from two different strategies. Either the heavy chain without the B-domain and the light chain are synthesized individually as two different polypeptide chains (two-chain strategy) or the B-domain deleted FVIII is synthesized as a single precursor polypeptide chain (single-chain strategy) that is cleaved into the heavy and light chains in the same way as the full-length FVIII precursor.

In a B-domain deleted FVIII precursor polypeptide, the heavy and light chain moieties are normally separated by a linker. To minimize the risk of introducing immunogenic epitopes in the B domain-deleted FVIII, the sequence of the linker is preferably derived from the FVIII B-domain. As a minimum, the linker must comprise a recognition site for the protease that separates the B-domain deleted FVIII precursor polypeptide into the heavy and light chain. In the B-domain of full length FVIII, amino acid 1644-1648 constitutes this recognition site. The thrombin site leading to removal of the linker on activation of B-domain deleted FVIII is located in the heavy chain. Thus, the size and amino acid sequence of the linker is unlikely to influence its removal from the remaining FVIII molecule by thrombin activation. Deletion of the B-domain is an advantage for production of FVIII. Nevertheless, parts of the B domain can be included in the linker without reducing the productivity. The negative effect of the B-domain on productivity has not been attributed to any specific size or sequence of the B-domain.

The truncated B-domain may contain several O-glycosylation sites. However, according to a preferred embodiment, the molecule comprises only one, alternatively two, three or four O-linked oligosaccharides in the truncated B-domain.

According to a preferred embodiment, the truncated B domain comprises only one potential O-glycosylation sites and a hydrophilic polymer is covalently conjugated to this O-glycosylation site. The O-linked oligosaccharides in the B-domain truncated molecules according to the invention may be attached to O-glycosylation sites that were either artificially created by recombinant means and/or by exposure of "hidden" O-glycosylation sites by truncation of the B-domain. In both cases, such molecules may be made by designing a B-domain truncated Factor VIII amino acid sequence and subsequently subjecting the amino acid sequence to an in silico analysis predicting the probability of O-glycosylation sites in the truncated B-domain. Molecules with a relatively high probability of having such glycosylation sites can be synthesized in a suitable host cell followed by analysis of the glycosylation pattern and subsequent selection of molecules having O-linked glycosylation in the truncated B-domain.

Suitable host cells for producing recombinant factor VIII protein are preferably of mammalian origin in order to ensure that the molecule is glycosylated. In practicing the present invention, the cells are mammalian cells, more preferably an established mammalian cell line, including, without limitation, CHO (e.g., ATCC CCL 61), COS-1 (e.g., ATCC CRL 1650), baby hamster kidney (BHK), and HEK293 (e.g., ATCC CRL 1573; Graham et al., J. Gen. Virol. 36:59-72, 1977) cell lines. A preferred BHK cell line is the tk-ts13 BHK cell line (Waechter and Baserga, Proc. Natl. Acad. Sci. USA 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk-ts13 BHK cell line is also available from the ATCC under accession number CRL 1632. A preferred CHO cell line is the CHO K1 cell line available from ATCC under accession number CCl61 as well as cell lines CHO-DXB11 and CHO-DG44.

Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1); DUKX cells (CHO cell line) (Urlaub and Chasin, Proc. Natl. Acad. Sci. USA 77:4216-4220, 1980) (DUKX cells also being referred to as DXB11 cells), and DG44 (CHO cell line) (Cell, 33: 405, 1983, and Somatic Cell and Molecular Genetics 12: 555, 1986). Also useful are 3T3 cells, Namalwa cells, myelomas and fusions of myelomas with other cells. In some embodiments, the cells may be mutant or recombinant cells, such as, e.g., cells that express a qualitatively or quantitatively different spectrum of enzymes that catalyze post-translational modification of proteins (e.g., glycosylation enzymes such as glycosyl transferases and/or glycosidases, or processing enzymes such as propeptides) than the cell type from which they were derived. DUKX cells (CHO cell line) are especially preferred.

Currently preferred cells are HEK293, COS, Chinese Hamster Ovary (CHO) cells, Baby Hamster Kidney (BHK) and myeloma cells, in particular Chinese Hamster Ovary (CHO) cells.

N-linked and O-linked oligosaccharides: Both N-glycans and O-glycans are attached to proteins by the cells producing the protein. The cellular N-glycosylation machinery recognizes and glycosylates N-glycosylation signals (N-X-S/T motifs) in the amino acid chain, as the nascent protein is translocated from the ribosome to the endoplasmic reticulum and continues until after transportation to the Golgi apparatus (Kiely et al., JBC (1976) 251(18), 5490; Glabe et al., JBC (1980)255(19), 9236, Lenting et al., Haemophilia (2010) 16(suppl.5), 194). N-linked FVIII oligosaccharide may be naturally occurring, which have been described in the art (Lenting et al., Haemophilia (2010) 16(Suppl 5), 194 and references cited herein), or it may be introduced by genetic engineering.

Likewise, O-glycans are attached to specific O-glycosylation sites. The commonly found mucin-type O-linked glycosylation involves the attachment of N-acetyl galactosamine moieties to Ser and Thr residues, a process that occurs when the protein has reached the Golgi apparatus. (Lenting et al. 2010.)

O-glycans are attached to specific O-glycosylation sites in the amino acid chain, but the motifs triggering O-glycosylation are much more heterogenous than the N-glycosylation signals, and our ability to predict O-glycosylation sites in amino acid sequences is still inadequate (Julenius et al., Glycobiology (2005), 15(2), 153 and Julenius et al., Bioinformatics for Glycobiology and Glycomics (2009) 163).

An O-linked oligosaccharide in a truncated Factor VIII B-domain may thus be covalently linked to a naturally occurring O-linked glycosylation sequence or an O-linked glycosylation sequence which has been artificially constructed by recombinant techniques.

An example thereof is a B-domain truncated Factor VIII variant wherein the B-domain corresponds to amino acids 742-763 in SEQ ID NO: 1. This variant comprises an O-glycosylation site in the B domain linker.

Another example is "N8", a B-domain deleted Factor VIII, the Factor VIII heavy chain comprising amino acid 1-740 of full length human Factor VIII, and Factor VIII light chain comprising amino acid 1649-2332 of full length human Factor VIII. The heavy and light chain sequences are connected by a 21 amino acid linker (SFSQNSRHPSQNPPV-LKRHQR—SEQ ID N0:2) comprising the sequence of amino acid 741-750 and 1638-1648 of full length human Factor VIII (Thim et al., Haemophilia (2010) 16, 349)

Sialyltransferase:

Sialyltransferases are enzymes that transfer sialic acid to nascent oligosaccharide. Each sialyltransferase is specific for a particular sugar substrate. Sialyltransferases add sialic acid to the terminal portions of the sialylated glycolipids (gangliosides) or to the N- or O-linked sugar chains of glycoproteins. There are about twenty different sialyltransferases which can be distinguished on the basis of the acceptor structure on which they act and on the type of sugar linkage they form. Preferred sialyltransferases according to the present invention are ST3Gal-I (specific for O-glycans) and ST3Gal-III (specific for N-glycans). It is thus possible to engineer the structure of the conjugated Factor VIII molecules according to the present invention by e.g., selection of a specific sialyltransferase and/or engineering of a Factor VIII molecule with a particular glycosylation pattern.

Glyco-Coniuqation of Polymers to O-Linked or (N)-Linked Oliqosaccharides:

The biosynthesis of O-glycans can be modified and terminated with the addition of sialic acid residues relatively early in biosynthesis. Certain sialyltransferase enzymes are capable of acting on GalNAcα-Ser/Thr, or early O-glycan core subtypes after Core 1 GalT action. The term T antigene is associated with the presence of the Galβ1-3GalNAcα-Ser/Thr disaccharide. Production of these structures involves a competition among glycosyltransferases for the same substrate and thus the expression levels and subcellular distributions of glycosyltransferases within the Golgi apparatus determine the structural outcome in O-glycan biosynthesis and diversification. Only the Galβ1-3GalNAcα-Ser/Thr disaccharide is amenable for glyco-derivatization However, the available amount of this structure may be greatly enhanced through treatment of the protein with a sialidase or Core1 GalT or a combination thereof. As a result of the process of glyco-conjugation of polymer the sialic acid polymer is added to the terminal Gal moiety through an α2,3 bond to the Galβ1-3GalNAcα-Ser/Thr disaccharide of the target protein (WO03031464 and WO09108806).

Many hydrophilic polymers can be attached to O-linked oligosaccharides. The basic requirement for enzymatically conjugating hydrophilic polymers to FVIII via the O-glycan is the ability to couple them to the cytidine monophosphate-5'-Glycyl-neuraminic acid (GSC) derivative via the free amino group as disclosed in WO03031464. This may be achieved through a large variety of coupling chemistries known to those skilled in the art. Examples of activated biocompatible polymer includes polyalkylene oxides such as without limitation polyethylene glycol (PEG), 2-(methacryloyloxy)ethyl phosphorylcholine (mPC) polymers (as described in WO03062290), dextrans, colominic acids or other carbohydrate based polymers, polymers of amino acids or of specific peptides sequences, biotin derivatives, polyvinyl alcohol (PVA), polycarboxylates, polyvinylpyrrolidone, polyethylene-co-maleic acid anhydride, polystyrene-co-malic acid anhydride, polyoxazoline, poly-acryloylmorpholine, heparin, albumin, celluloses, hydrolysates of chitosan, starches such as hydroxyethyl-starches and hydroxy propyl-starches, glycogen, agaroses and derivatives thereof, guar gum, pullulan, inulin, xanthan gum, carrageenan, pectin, alginic acid hydrolysates, other bio-polymers and any equivalents thereof.

Side groups can be attached to N-linked oligosaccharides by sialyltransferase mediated methods as disclosed in e.g., WO0331464. Such methods frequently result in attachment of several side groups to the Factor VIII molecule.

Side groups attached to N-linked oligosaccharides of FVIII will be described as (N)-side group FVIII. Side groups attached to O-linked oligosaccharides will be described as (O)-side group FVIII. For example, (O)-PEG(40 kD) (N)-PSA(20 kD) FVIII means that PEG(40 KD) is attached to O-linked oligosaccharides, and PSA(20 kD) is attached to N-linked oligosaccharides.

Chemical Conjugation:

The FVIII variants according to the present invention may be conjugated with PEG and polysaccharide polymers using various chemo-enzymatic methods.

Chemical conjugation of relevant moieties to drugs has usually employed techniques like random derivatization of lysine residues by acylation or reductive alkylation, but the utility of these methods is generally limited, due to heterogeneicity of the product and the most often decreased bioactivity of the products obtained.

Site-selective conjugation methods are essential to be able to exploit the protein structural and biological knowledge available to choose sites which will not affect the protein biological activity, and at the same time obtain the desired effect on stability, pharmacokinetic parameters, immunogenicity, binding to biological partners etc.

N-terminal specific, or at least N-terminal preferential conjugation, can be achieved using the fact that the N-terminal primary amino has a pKa of 7.8, whereas that of the c-amino groups of lysine side chain is much higher.

A more narrow application method uses the introduction of a glyoxyl group at the amino-terminus of a protein. It is however restricted to proteins which can tolerate a harsh periodate oxidation reaction and which contain N-terminal serine or threonine residues.

Thiol selective conjugation to an unpaired cysteine residue is potentially also a useful procedure to achieve site-selective conjugation using a maleimide or haloacetate derivative of the relevant moiety to conjugate. The conjugation can be done on:

either a naturally free cysteine—free cysteine are rare residues in proteins—but since cysteine is a quite hydrophobic amino acid, it is often buried inside the protein structure, and thus poorly accessible to reagents;

or, more likely, a cysteine residue introduced into the protein by site-directed mutagenesis, but with all the potential problems of possible protein structure change and immunogenicity.

Enzymatic conjugation methods are also used and can be a valuable tool for accessing a restricted number of amino acid residues in a protein. For example, out of the thirteen glutamine residues of the human growth hormone, only two are substrates for the microbial transglutaminase enzyme (WO06/134148). (Fontana et al., Adv. Drug Delivery Rev. (2008) 60, 13-28 and references cited therein, Bonora et al. (2009), Post-translational Modification of Protein Biopharmaceuticals, Wiley, 341 and references cited therein).

PEG: The term "PEG" in connection with the present invention includes poly(ethylene glycol) in any of its forms, including alkoxy PEG, difunctional PEG, multiarmed PEG, forked PEG, branched PEG, pendent PEG (i.e., PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine or cysteine. In one example, the branched poly(ethylene glycol) can be represented in general form as R(-PEG-OH)m in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Although the molecular weight of each chain of the polymer backbone can vary, it is typically in the range of from about 100 Da to about 160,000 Da, such as e.g. from about 5,000 Da to about 100,000 Da. More specifically, the size of each conjugated hydrophilic polymer according to the present invention may vary from about 500 Da to about 80,000 Da, such as e.g. about 1000 Da to about 80,000 Da; about 2000 Da to about 70,000 Da; about 5000 to about 70,000 Da; about 5000 to about 60,000 Da; about 10,000 to about 70,000 Da; about 20,000 to about 60,000 Da; about 30,000 to about 60,000 Da; about 30,000 to about 50,000 Da; or about 30,000 to about 40,000 Da. It should be understood that these sizes represent estimates rather than exact measures. According to a preferred embodiment, the molecules according to the invention are conjugated with a heterogenous population of hydrophilic polymers, such as e.g., PEG of a size of e.g., 10,000, 40,000, or 80,000 Da+/−about 5000, about 4000, about 3000, about 2000, or about 1000 Da.

Polysaccharide

A polysaccharide in connection with the present invention is a polymer based on polysaccharides, including homo- or hetero-polysaccharides, consisting of monomers units like glucose, galactose, sulfo-galactose, N-acetyl-galactose, fucose, fructose, xylose, arabinose, glucuronic acid, sulfo-glucuronic acid, iduronic acid, sulfo-iduronic acid, galacturonic acid, mannuronic acid, glucosamine, N-acetyl-glucosamine, sulfo-glucosamine, galactosamine, N-acetyl-galactosamine, N-acetyl-galactosamine-sulfate, N-acetyl-galactosamine-disulfate N-acetyl-galactosamine-sulfate, N-acetyl-neuraminic acid (Neu5Ac), Sulfo-N-acetyl-neuraminic acid, N-glycolyl-neuraminic acid (Neu5Gc), 2-keto-3-deoxy-nonulosonic acid (KDN).

Examples of polysaccharides in connection with the present invention include: lactose, starch, hydroxyethyl starch (HES), amylase, dextran sulfate, dextran, dextrins, glycogen, hyaluronic acid, polysorbitol, polymannitol, heparin, heparan sulfate, chondroitin sulfate, dermatan sulfate, keratin sulphate, heparin or chondroitin sulphate, sulfated polysialic acid and polysialic acid (PSA).

A preferred polysaccharide according to the invention is PSA. PSA is a polymer which is present in mammals, i.e. it is not (or very weakly) immunogenic. There are no known PSA receptors in mammals. PSA has been shown to provide therapeutic proteins with increased resistance to protease degradation. Preferably, most or all of the saccharide residues are N-acetyl-neuraminic acid (Neu5Ac) residues, preferably only Neu5Ac residues. Polysialic acids produced by bacteria are preferred sources of polysialic acids. They include the serogroup C capsular polysaccharide C from *N. meningitidis* C and the polysaccharide K92 from *E. coli* K92, and the serogroup B capsular polysaccharide from *Neisseria meningitidis* B and *Escherichia coli* K1, *Moraxella nonliquifaciens*, *Mannheimia haemolytica* A2 (formerly known as *Pasteurella haemolytica* A2). The polysaccharide from *E. coli* K92 comprises alternating alpha2,8 and alpha2,9 linked Neu5Ac units. Polysaccharide C from *N. meningitidis* group C has alpha2,9 linked Neu5Ac units. The preferred polysialic acids are from group B; they comprise 2,8-alpha linked Neu5Ac. The molecular weight of the PSA is preferably higher than or equal to 20 kDa, 25 kDa, 30 kDa, 35 kDa, 40 kDa 45 kDa, 50 kDa, 55 kDa, 60 kDa, 65 kDa, 70 kDa, 75 kDa, 80 kDa, 85 kDa, 90 kDa, 95 kDa, or 100 kDa. PSA polymers in connection with the present invention are preferably of a narrow molecular weight distribution.

In the method of the present invention, the reactive aldehyde of the PSA is preferably at the non-reducing end of the polysaccharide. However, the reactive aldehyde may also be provided at the reducing end, as described in U.S. Pat. No. 4,356,170 for example.

In another aspect of the invention, the polysialylated moiety may be generated enzymatically, using a combination of a sialyltransferase and a polysialyltransferase. The sialyltransferase is preferably the *Campylobacter jejuni* sialyltransferase CstII (Gilbert et al. JBC (2002) 277, 327) using either the (O)-asialo glycan of N8 as the substrate, or the complex type (N)-glycans of N8 as the substrate.

The resulting glycans carrying an alpha2,3-alpha2,8 linked disialyl end motif can then be used as the substrate for a bacterial polysialyltransferase like the alpha2,8-polysialyltransferase of *N. meningitidis* or *E. coli* K1 (Willis et al., Glycobiology (2008) 18(2) 177, WO 2008/151448 A1, Cho and Troy, PNAS (1994), 91, 11427).

Alternatively, the polysialylated moiety may be generated enzymatically, using a fusion protein comprising a bifunctional sialyltransferase and a polysialyltransferase, as described in WO 2007/087711 A1. Alternatively, the polysialylated moiety may be generated enzymatically using mammalian alpha2,8-polysialyltransferases like STX (ST8Sia II) and/or PST (ST8Sia IV) using (N)-glycans of N8 as the substrate (Angata et al. JBC 277(39)36808 and references cited therein).

Pharmaceutical Composition:

A pharmaceutical composition is herein preferably meant to encompass compositions comprising Factor VIIII antibodies according to the present invention optionally in combination with Factor VIII molecules suitable for parenteral administration, such as e.g., ready-to-use sterile aqueous compositions or dry sterile compositions that can be reconstituted in e.g. water or an aqueous buffer. The compositions according to the invention may comprise various pharmaceutically acceptable excipients, stabilizers, etc.

Additional ingredients in such compositions may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention. Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the FVIII antibody compound in the form of a nasal or pulmonal spray. As a still further option, the pharmaceutical compositions containing the FVIII compound of the invention may also be adapted to transdermal administration, e.g., by needle-free injection or from a patch, optionally an iontophoretic patch, or transmucosal, e.g., buccal, administration.

The term "treatment", as used herein, refers to the medical therapy of any human or other animal subject in need thereof. Said subject is expected to have undergone physical examination by a medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Thus, said treatment may be prophylactic, palliative, and/or symptomatic.

While certain features of the invention have been illustrated and described herein, many modifications, substitutions, changes, and equivalents will now occur to those of ordinary skilled in the art. It is, therefore, to be understood that the appended claims are intended to cover all such modifications and changes as fall within the true spirit of the invention.

In a first aspect, the present invention relates to a FVIII variant conjugated with at least one PEG polymer and at least one polysaccharide. Such "heteroconjugated" variants surprisingly have an in vivo circulatory half life that is improved in comparison with "homo-conjugated" FVIII variants (e.g., FVIII-PEG-PEG or FVIII-PSA-PSA variants).

In one embodiment of the present invention, the polysaccharide is PSA.

In another embodiment, said FVIII variant according to the invention is a B-domain truncated molecule covalently conjugated with a PEG polymer or a PSA polymer via an O-linked oligosaccharide in the truncated B-domain, wherein FVIII activation results in removal of said O-linked polymer.

In another embodiment, said variant is covalently conjugated with at least one PEG polymer or a PSA polymer via an N-linked oligosaccharide. This N-linked oligosaccharide may be naturally occurring or it may be introduced by genetic engineering.

In another embodiment, said FVIII variant is covalently conjugated with a PEG polymer via an O-linked oligosaccharide in the truncated B-domain and wherein said variant is covalently conjugated with at least one PSA polymer via an N-linked oligosaccharide. In its activated stage, this FVIII variant may be similar to endogenous activated FVIII if the polymeric groups are conjugated to glycans in the B-domain.

In another embodiment, said FVIII variant comprises two to four PSA polymers linked to one double-branched N-linked oligosaccharide in the A1 domain and one double-branched N-linked oligosaccharide in the A3 domain.

In another embodiment, said FVIII variant is covalently conjugated with at least one PEG polymer or a PSA polymer via an N-linked oligosaccharide.

In another embodiment, said FVIII variant is covalently conjugated with a PEG polymer via the O-linked oligosaccharide in the truncated B-domain and wherein said variant is covalently conjugated with at least one PSA polymer via an N-linked oligosaccharide.

In another embodiment, said FVIII variant comprises two to four PSA polymers linked to one double-branched N-linked oligosaccharide in the A1 domain and one double-branched N-linked oligosaccharide in the A3 domain.

In one embodiment, said FVIII variant comprises one or two PSA polymers linked to one double-branched N-linked oligosaccharide in the A1 domain.

In one embodiment, said FVIII variant comprises one or two PSA polymers linked to one double-branched N-linked oligosaccharide in the A3 domain.

In one embodiment, said FVIII variant is covalently conjugated with a PSA polymer via the O-linked oligosaccharide in the truncated B-domain and wherein said variant is covalently conjugated with at least one PEG polymer via an N-linked oligosaccharide.

In one embodiment, said FVIII variant is covalently conjugated with a PEG polymer via the O-linked oligosaccharide in the truncated B-domain and wherein said variant is covalently conjugated with at least one PSA polymer via an N-linked oligosaccharide.

In one embodiment, said FVIII variant comprises two to four PEG polymers linked to one double-branched N-linked oligosaccharide in the A1 domain and one double-branched N-linked oligosaccharide in the A3 domain.

In one embodiment, said FVIII variant comprises one to two PEG polymers linked to one double-branched N-linked oligosaccharide in the A1 domain.

In one embodiment, said FVIII variant comprises one to two PEG polymers linked to one double-branched N-linked oligosaccharide in the A3 domain.

In another embodiment, said FVIII variant comprises a PEG polymer having a size of 30-50 kDa.

In another embodiment, said FVIII variant comprises a PSA polymer having a size of 15-50 kDa.

In another embodiment, said FVIII variant comprises a PSA polymer having a size of 40-50 kDa.

In another embodiment, said FVIII variant is a B-domain truncated FVIII variant, wherein the B-domain comprises the amino acid sequence as set forth in SEQ ID NO:2.

In another embodiment, the polysaccharide is hydroxyethyl starch (HES).

A second aspect relates to a method of making a FVIII variant according to the invention, wherein said method comprises conjugating a FVIII molecule with at least one PEG polymer and at least one polysaccharide.

In one embodiment, at least one of the conjugation steps in said method is an enzymatic process.

A third aspect relates to FVIII variants obtained by or obtainable by a method according to the invention.

A fourth aspect relates to a pharmaceutical composition comprising a FVIII variant according to the invention and optionally one or more pharmaceutically acceptable excipients. Such composition is preferably intended for IV or subcutaneous administration.

A fifth aspect relates to use of a FVIII variant or a pharmaceutical composition according to the invention as a medicament.

A sixth aspect relates to use of a FVIII variant or a pharmaceutical composition according to the invention as a medicament for treating haemophilia A.

A seventh aspect relates to a method of treating haemophilia A comprising administering a therapeutically effective amount of a FVIII variant or pharmaceutical composition according to the invention to a patient.

EXAMPLES

Abbreviations

DIC: Diisopropyl carbodiimide
HOBt: 1-Hydroxy-benzotriazole
THF: Tetrahydrofuran
DCM: Dichloromethane
DMF: Dimethyl formamide
TFA: Trifluoro acetic acid
HC, LC: Heavy and Light Chains of N8
CMP: Cytidine monophosphate
GSC: Cytidine monophosphate-5'-Glycyl-neuraminic acid
GSC-ONH$_2$: 5'-(2-(12-((aminoxymethylcarbonyl)amino)-4,7,10-trioxadodecanoyl)-aminoethanoyl) neuraminic acid cytidine monophosphate
HOAt: 1-Hydroxy-7-aza-benzotriazole
PSA: Polysialic acid. Exemplified here with α2,8-polysialic acid (colominic acid)
NAN-CMP: N-acetyl neuraminic acid cytidine monophosphate
SEC-MALS: Size-exclusion chromatography with Multi-Angle-Light Scattering detection.
IEX: Ion exchange
CV: Column volume Synthesis of N8 Conjugates of the Type (O)-PEG40 (N)-PSA-N8

General description: a commercial colominic acid was fractionated on anion exchange column, and the fractions having a molecular weight of either about 20 kD or about 45 kD were pooled. The obtained material was oxidized with sodium periodate. The oxidized PSA was coupled to the GSC-hydroxylamine derivative 5'-(2-(12-((aminoxymethylcarbonyl)amino)-4-7-10-trioxadodecanoyl)aminoethanoylneuraminic acid cytidine monophosphate to give the GSC-ON=PSA re-agent which was used as the donor in the ST3Gal-III catalyzed polysialylation of N-asialo (O)-PEG40 N8 (PSA was thus coupled on N-glycans).

A detailed description of the synthesis of the conjugates of this type is given below:

Example 1

Synthesis of 12-((Fmoc-aminoxymethylcarbonyl)amino)-4-7-10-trioxadodecanoic acid 3

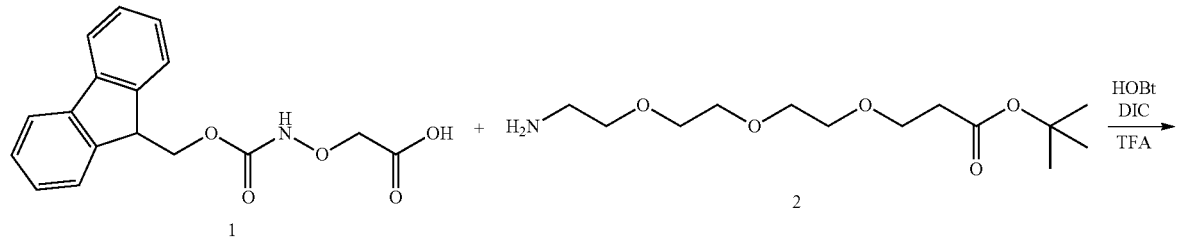

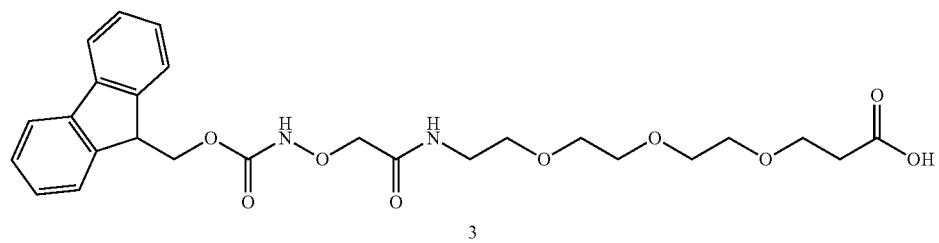

Fmoc-aminoxyacetic acid 1 (1000 mg, 3.2 mmol), 12-amino-4-7-10-trioxadodecanoate t-butyl ester 2 (885 mg; 3.2 mmol), and HOBt (431.5 mg; 3.2 mmol) were solubilized in THF (5 ml). DIC (402 mg; 3.2 mmol) was then added. The mixture was stirred overnight at ambient temperature.

LC-MS analysis showed that the desired product had been formed (m/z=574).

The reaction mixture was partitioned between DCM and sodium hydrogenocarbonate. The organic phase was washed twice with sodium hydrogenocarbonate, dried on sodium sulfate and evaporated.

The residue was dissolved in 20% TFA-DCM (10 ml), stirred at ambient temperature for 30 min, and evaporated. LC-MS analysis showed the presence of the desired product 12-((Fmoc-aminoxymethylcarbonyl)amino)-4-7-10-trioxaundecanoic acid 3 (m/z=517).

The oily residue was purified by flash chromatography on silica, using solvents A: DCM and solvent B: 5% $CH_3OH$ in DCM, at a flow rate of 40 ml/min. The gradient was: 0% B over 0.5 CV, o to 100% B over 11.5 CV, 100% B over 2.5 CV. The product eluted between 90 and 100% B. The relevant fractions were checked on TLC, and the pure fractions pooled and evaporated, giving colorless oil with a yield of 75%.

LC-MS: m/z=517

$^1$H-NMR ($CDCl_3$; 400 MHz): δ 2.55 ppm (t, 2H); 3.45-3.75 (m, 10H); 4.22 (t, 1H); 4.42 (s, 2H); 4.52 (d, 2H); 7.32 (t, 2H); 7.41 (t, 2H); 7.57 (d, 2H); 7.75 (d, 2H); 8.07 (bs, 1H); 8.79 (bs, 1H).

Example 2

Synthesis of the GSC Derivative: (5'-(2-(12-((aminoxymethylcarbonyl)amino)-4-7-10-trioxadodecanoyl)-aminoethanoyl)-neuraminic Acid cytidine monophosphate) 6 ("GSC-ONH$_2$")

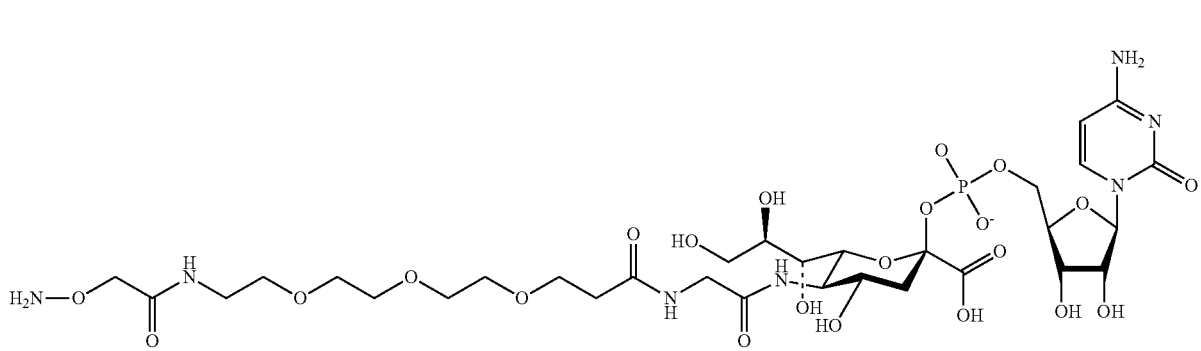

1st step:

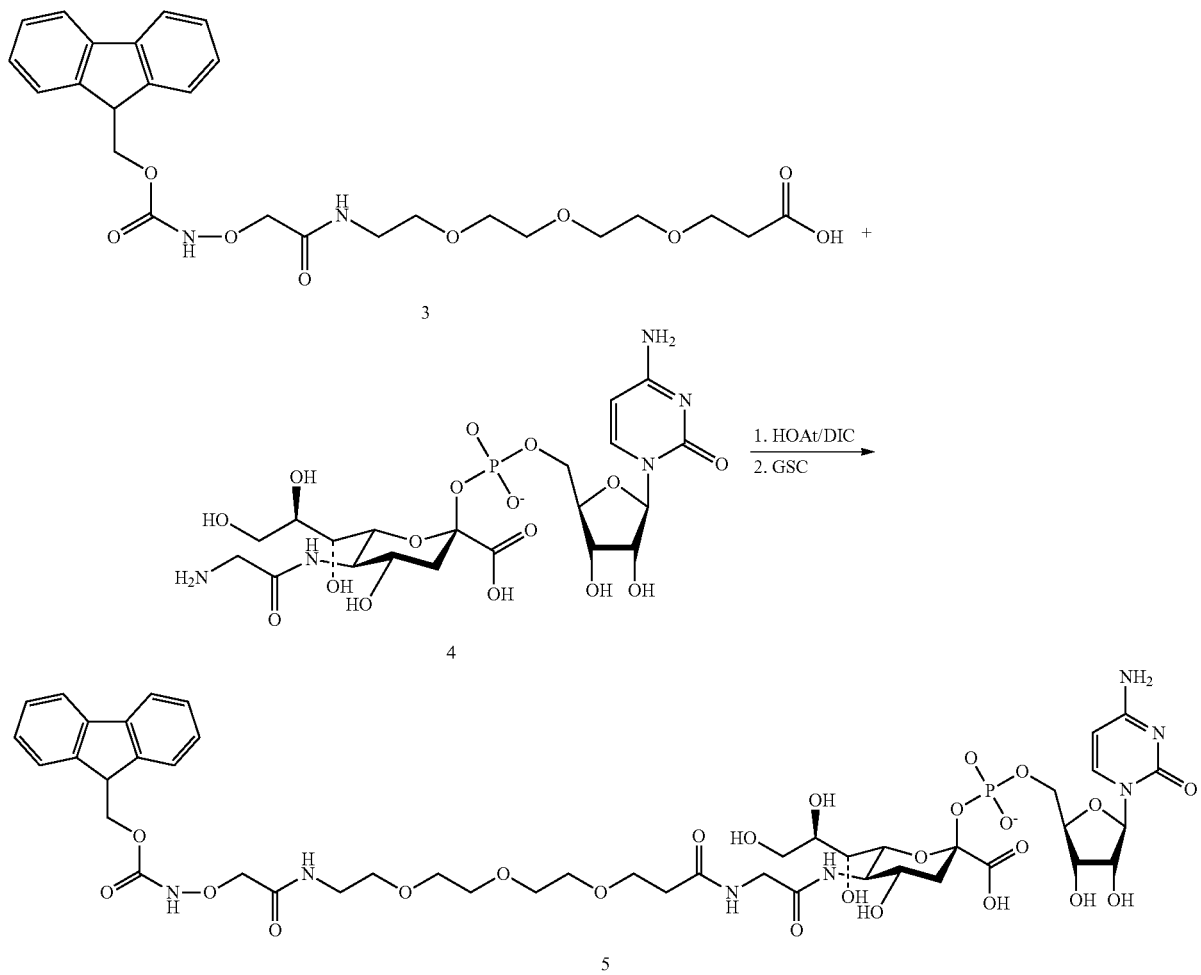

To a solution of the carboxylic acid 3 (0.52 g, 1 mmol) in dry THF (5 ml) are added HOAt (2.2 ml, 1.1 equiv of a 0.5M solution in NMP) and DIC (0.205 ml, 1.3 mmol, 1.3 equiv). The reaction mixture was stirred for 0.5 h at ambient temperature.

The same amount of DIC was then added, followed by a freshly prepared solution of GSC 4 (0.69 g, 1.1 mmol) in aqueous 100 mM HEPES buffer (10 ml). The reaction mixture turned yellow. A further addition of DIC (1.1 equiv) was done after 5.5 h reaction time.

The reaction mixture was then incubated overnight at ambient temperature.

LC-MS analysis showed that the expected product 5 had been formed (m/z=1128.7).

The reaction mixture was filtered through a PTFE filter, and purified by HPLC on a reverse phase C18 column using acetonitrile and 250 mM ammonium hydrogen carbonate as solvents. The relevant fractions were pooled and lyophilized. The purity was checked before and after lyophilization by analytical HPLC, on a reverse phase C18 column (Waters Symmetry C18, 5μ, 3.9×150 mm), using the solvents A: acetonitrile, B: $H_2O$, C: 0.5 M $NH_4HCO_3$ pH 7.9. The linear gradient started with a mixture of B:C (90:10) and ended with a mixture A:B:C: (60:30:10) over 15 min, at a flow rate of 1 ml/min. The column oven was set at a temperature of 42° C. A minor decomposition occurred under lyophilisation (less than 4%).

Ammonium cations were then exchanged to sodium using a Dowex 50 W resin as follows: Dowex 50 W×2, 100-200 mesh (H+ form) (12 g) was placed in a 20 ml filter syringe. The resin was washed with 1N NaOH until the eluate was basic (25 ml). The resin was then washed with water until the eluate was pH-neutral. The product was dissolved in THF: $H_2O$ (1:10) (11 ml), applied on the resin, and eluted dropwise (7×5 ml $H_2O$). The fractions were spottet on TLC (Mercks Silica gel 60 $F_{254}$ nm); relevant fractions were pooled and lyophilized.

The product was quantified on an HPLC equipped with a nitrogen detector, running the product on a reverse phase Phenomenex Jupiter C18 100×4.6 mm, 5μ, 300 Å column.

The solvents were A: $H_2O$, B: 2-propanol, C: 1% TFA. The gradient started with a mixture of A:C (90:10), and ended with a mixture (A:B:C) (10:80:10), The flow was 1 ml/min. The yield was 46%.

2nd Step:
The product was then deprotected with dimethylamine:

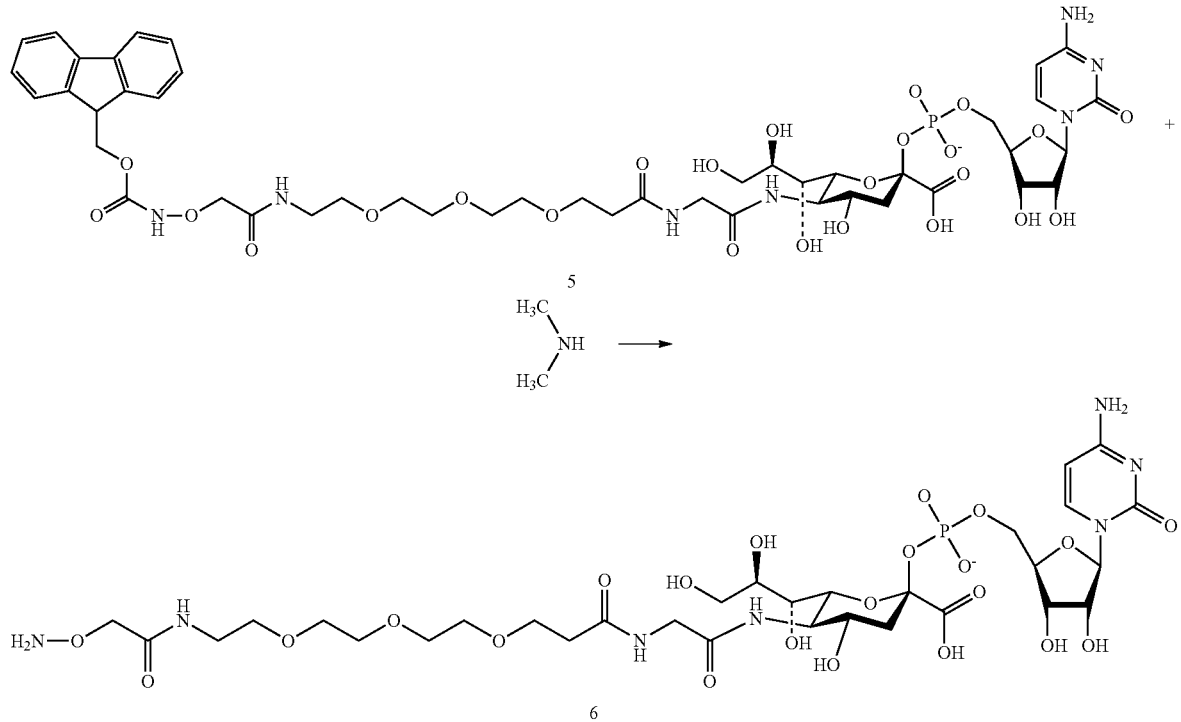

5 (200 mg) was dissolved in 10% aqueous methanol (3.3 ml). Dimethylamine (3 ml of a 40% solution in H₂O), and the reaction mixture stirred for 1.5 h at ambient temperature. The mixture became cloudy after 10-15 min. The reaction was monitored by LC-MS. The reaction was completed after 1 h at 20° C.

The reaction mixture was diluted with water (5 ml) and washed with dichloromethane (4×5 ml). Both phases were checked on LC-MS. The aqueous phase contained the product, and the fluorene moiety could not be detected. In the organic phase, no product could be detected. The aqueous phase was lyophilized, giving the GSC derivative 5'-(2-(12-((aminoxymethylcarbonyl)amino)-4-7-10-trioxadodecanoyl)aminoethanoyl)-neuraminic acid cytidine monophosphate ("GSC-ONH₂") 6 as a colorless solid.

Example 3

Colominic Acid Fractionation to Get a Material of about 20 kDa in Molecular Weight The colominic acid used was the commercial compound from Sigma-Aldrich (α2,8 polysialic acid sodium salt, (PSA) from *Escherichia coli*). In order to get a more homogenous material (regarding its molecular weight), it was fractionated on an ion exchange column according to WO 2008/074032. The fraction corresponding to a molecular weight of about 20 kD was used in the subsequent experiments.

Example 4

Sodium Periodate Oxidation of the 20 kD PSA Material Isolated in Example 3

The sodium periodate oxidation of the polyol at the non reducing end of the PSA polymer was performed essentially as described in the literature (for example: Jain and al., BBA (2003) 1622, 42-49), with some modifications To a solution of 20 kD PSA (40 mg in 2.24 ml H₂O) was added a sodium periodate solution (0.96 mg in 2.244 ml H₂O). The reaction was incubated for 15 min at 23° C. in the dark.

The excess of periodate was quenched by 3-methylthio-1-propanol (4.7 μl). The reaction was further incubated for 2 h at 23° C.

The reaction mixture was buffer shifted to water by ultra filtration on Millipore Ultra, 5 kD cut-off and lyophilized. The lyophilized material was used as such in the next step, where it was reacted with GSC-ONH₂.

Example 5

Coupling of Sodium Periodate Oxidized PSA(20 kD) to GSC-ONH₂ to Yield the Sialyltransferase ST3GalIII Substrate GSC-ON=PSA(20 kD)

Solutions
  Reaction buffer: 100 mM imidazole pH 6.8
  GSC-ONH₂ (from example X2): 8.2 mg/ml in reaction buffer
  Periodate oxidized PSA(20 kD): 175 mg/ml in reaction buffer
  aniline (MW=93.13, d=1.0217)
  Methylhydroxylamine hydrochloride: 58.5 mg/ml in reaction buffer.

Procedure:
  To the periodate oxidized PSA(20 kD) solution in reaction buffer (200 μl, 35 mg, 1.75 μmole) was added the GSC-ONH₂ solution in reaction buffer (400 μl, 3.26 mg, 3.6 μmoles, about 2 equiv.). The pH was adjusted to 6.9 by addition of 1 M HCl (5.5 μl) under vigorous magnetic stirring. Aniline (0.56 μl, 6 nmoles) was then added. The yellowish and slightly cloudy mixture was incubated at 25° C. Some precipitation was observed after 10-15 min.

The reaction progress was followed by analysis on a size exclusion column Waters Biosuite 125, HR ESC 300×7.8 mm (+guard column), with 100 mM phosphate buffer pH 6.8 buffer as eluent, a flow of 0.6 ml/min, at ambient temperature, with a DAD detector at 212 and 272 nm. An analysis was run after 30 min, 2 h and 18 h reaction time.

GSC-ONH$_2$ elutes at 18.5 min in this system. The product elutes as a broad "peak" at a retention time of about 13.8 min.

Since both PSA(20 kD) and the product GSC-ON=PSA(20 kD) elute at the same retention time, the progress of the reaction was monitored by looking at the ratio: (area of product peak at 272 nm) over (area of product peak at 212 nm) (PSA absorbs only at 212 nm, GSC absorbs at 272 nm). The ratio increased from 30 min to 2 h, and remained constant until 18 h reaction time.

After 19 h reaction time, any unreacted aldehyde was quenched by addition of the methylhydroxylamine solution, (25 µl, 10 equiv), and the mixture incubated for 1 h at ambient temperature.

The reaction mixture was then filtered on 0.45µ filter (Millipore Millex-HV (PVDF)), and further purified on ProSpin CS-800 (Princeton Separations) conditioned in 1.5 g/l L-Histidine, 3 g/l Sucrose, 18 g/l NaCl, 0.1 g/l TWEEN® 80; 0.25 g/l CaCl$_2$, 2H$_2$O, pH7.3 buffer, to get rid of low molecular weight re-agents.

The quantification of the final product was done relative to CMP (Sigma C1006): a standard curve was done by measuring the absorption of CMP solutions of known concentrations at 272 nm.

GSC-ON=PSA(20 kD) was obtained with a yield of 45% relative to periodate oxidized PSA.

Example 6

Preparation of (N)-PSA (20 kD)-(O)-PEG (40 kD)-N8 by Sialyltransferase ST3Gal-III Catalyzed Reaction of (N)-asialo (O)-PEG(40 kD) N8 with GSC-ON=PSA(20 kD)

1st step:
(O)-PEG(40 kD) (N)-asialo-N8 N8

The compound was synthesized according to the procedure disclosed in Patent WO2009/108806 A1.

2nd step:
ST3Gal-III catalyzed PSAylation of (O)-PEG(40 kD) (N)-asialo N8 with GSC-ON=PSA(20 kD):

Solutions:
Reaction buffer: 1.5 g/l L-Histidine, 3 g/l Sucrose, 18 g/l NaCl, 0.1 g/l Tween 80; 0.25 g/l CaCl$_2$, 2H$_2$O, pH 7.3
GSC-ON=PSA(20 kD): 0.78 mM in reaction buffer
ST3Gal-III: (rat enzyme): 1.42 mg/ml (1.34 U/mg)
(O)-PEG(40 kD)-(N)-asialo N8: 1.76 mg/ml in reaction buffer Procedure:
To the (O)-PEG(40 kD) (N)-asialo N8 solution (272 µl, 0.48 mg protein, 2.71 nmoles) was added the GSC-ON=PSA solution (36.5 µl, 28.5 nmoles, 10.5 equiv). Reaction buffer (104 µl) was added. The reaction was started by addition of the enzyme (63.2 µl, 89.6 µg, about 120 mU). The reaction mixture was incubated at 32° C. for 22 h.

The product was capped by addition of a solution of NAN-CMP (1 mg) in 10 µl reaction buffer. The reaction mixture was incubated for 1 h at 32° C.

Work-Up and Purification:
The buffers used were:
Buffer A: 20 mM imidazole buffer pH 7.4 containing 10 mM CaCl$_2$, 1 M glycerol, 0.02% TWEEN80, without NaCl
Buffer B. buffer A+1M NaCl
Reaction buffer: 1.5 g/l L-Histidine, 3 g/l Sucrose, 18 g/l NaCl, 0.1 g/l TWEEN 80, 0.25 g/l CaCl$_2$, 2H$_2$O, pH7.3

Work-Up and Purification:
After dilution in buffer A (8 ml), the reaction mixture was purified by ion exchange on a Vivapure Q Mini M device according to the manufacturer instructions. The product was recovered in buffer B.

The product was further run on the size exclusion column SUPERDEX® 200 10×300 GL (GE Healthcare), using the reaction buffer as eluent.

The protein recovery was 32%.

Product Characterization:
SDS PAGE Analysis:
The recovered product was run on a 7% Tris-acetate SDS gel (150V, 1 h10) (Invitrogen) under reducing conditions, using Coomassie blue staining. The protein standard was the HiMark unstained HMW Protein Standard from Invitrogen.

The pegylated heavy chain band of (O)-PEG (40 kD) (N)-asialo N8, appeared at about 240 kD and the light chain at about 83 kD. After PSAylation, a band assumed to correspond to the PSAylated heavy chain appeared at a higher MW, (between 260 and 280 kD, as expected. In addition, a wide and diffuse band, assumed to correspond to the PSAylated light chain, appeared at between 97 and 116 kD.

No remaining band corresponding to the heavy chain of N8 could be detected, and only traces of the light chain could be seen, showing that PSA was indeed transferred on both heavy and light chain of (O)-PEG40 kD-N8.

Analysis on Reverse Phase HPLC:
The analysis was run on a reverse phase Daiso 300 Å, 250×2.1, 5µ column. The eluents were: A: H$_2$O/TFA 0.1%, and B: H$_2$O/ACN/TFA (80:20:0.09%), the flow 0.25 ml/min, and the temperature of the column oven 40° C. The gradient was from 35% to 84% over 30 min. The HPLC was equipped with two detectors: a DAD detector (280 nm) and a fluorescence detector with the excitation wavelength at 280 nm, and the emission wavelength at 348 nm. The retention times of the heavy chain and light chain of the product were as indicated in the table below. The retention times of the heavy chain and light chain of FVIII and of the intermediate (O)-PEG (40 kD)-N8 are indicated for comparison:

| | Sample | | |
|---|---|---|---|
| Rt | N8 | (O)-PEG(40 kD) N8- | (O)-PEG(40 kD) (N)-PSA(20 kD)-N8- |
| Rt LC | 19.98 min | 19.95 min | 19.85 min |
| Rt HC | 24.35 min | 23.84 min | 23.64 min |

Thus, as expected for the more polar final product [(N)-PSA (20 kD)-(O)-PEG (40 kD) N8], the retention times of the heavy and light chains are shorter than the retention times for the HC and LC of the starting and intermediate compounds. It is somewhat surprising that one does not obtain a larger effect on the retention time after coupling of the polysialic acid. But the system does not reflect physiological conditions, as the acid present in the eluent is neutralizing the negative charge from the carboxylic acids moieties of PSA.

Activity:

The activity of the final product was measured in the chromogenic assay CoA test SP FVIII from Chromogenix: compared to the starting FVIII, more than 80% of the activity was recovered.

Example 7

Colominic Acid Fragmentation to Get a Material of about 45 kD in Molecular Weight The colominic acid used was the commercial compound from Sigma-Aldrich (α2,8 polysialic acid sodium salt, (PSA)). In order to get a more homogenous material (regarding its molecular weight), it was fractionated on a HiPrep 16/10 Q FF anion exchange column (GE Healthcare) using buffers A and B:
A: 10 mM Triethanol amine pH7.4, 25 mM NaCl
B: 10 mM Triethanol amine pH7.4, 1 M NaCl After equilibration of the column with 8CV of buffer A, the colominic acid was fractionated (5 ml fractions) using a gradient from 17.5% to 100% B over 24 CV with a flow of 2 ml/min. The UV detection was at 210 nm. The fractions were buffer shifted to water by ultrafiltration on Millipore Amicon Ultra 3 kD cut-off, lyophilized, and analysed by SEC-MALS and UV. The fractions corresponding to a molecular weight of about 45 kD (molecular weight at maximum UV absorption), with a molecular weight range of 38-77 kD ("45 kD PSA") were pooled and used in the subsequent experiments.

Example 8

Sodium Periodate Oxidation of 45 kD PSA

To an aqueous solution of the material obtained in example 7("45 kD PSA") (13.5 mg in 0.5 ml water) was added a 4 mM aqueous sodium periodate solution (167 µl, 2.24 molar equivalents). The reaction was incubated for 15 min at ambient temperature in the dark. The excess of sodium periodate was quenched by 3-methylthio-1-propanol (0.7 µl, 12 molar equivalents). The reaction was further incubated for 2 h at ambient temperature. The reaction mixture was buffer shifted to water by ultra filtration on Millipore Amicon Ultra-4, 5 kD cut-off and lyophilized. The lyophilized material was used as such in the next step.

Example 9

Coupling of Sodium Periodate Oxidized PSA(45 kD) to GSC-ONH$_2$ to Yield the Sialyltransferase ST3GalIII Substrate GSC-ON=PSA(45 kD)

Solutions:
Reaction buffer: 100 mM imidazole pH 6.8
GSC-ONH$_2$ (from example 2): 8.3 mg/ml in reaction buffer (pH adjusted to 6.8)
Periodate oxidized 45 kDa PSA (from example Y2): 355 mg/ml in reaction buffer
saturated aqueous aniline solution (about 0.38 M)
Methylhydroxylamine hydrochloride: 58.5 mg/ml in reaction buffer
Procedure:

The reaction is run essentially as described in example 5. The detailed description is included below: To the periodate oxidized 45 kD PSA (from example 8) solution in reaction buffer (92 µl, 32.7 mg, 0.73 µmole) was added the GSC-ONH$_2$ (from example 2) solution in reaction buffer (168 µl, 1.4 mg, 1.5 µmoles, about 2 equiv.). Saturated aqueous solution of aniline (6.8 µl, 2.58 µmoles) was then added. The reaction mixture was incubated at ambient temperature.

The reaction progress was followed by HPLC analysis using a size exclusion column Waters Biosuite 125, HR ESC 300×7.8 mm (+guard column). The eluent was 100 mM phosphate buffer pH 6.8 buffer, the flow was 0.6 ml/min. The analysis was run at ambient temperature, with a DAD detector at 214 (PSA and GSC moiety detection) and 272 nm (GSC moiety detection). GSC-ONH$_2$ eluted at 18.5 min, the oxidized 45 kD PSA and the reaction product eluted at the same retention time of 10.3 min.

Since both oxidized 45 kD PSA and the product GSC-ON=PSA elute at the same retention time, the progress of the reaction was monitored by looking at the ratio: (area of oxidized 45 kD PSA/GSC-ON=PSA peak at 272 nm) over (area of oxidized 45 kD PSA/GSC-ON=PSA at 212 nm).

An analysis was run after 1 h, 1 h45, 3 h, 4 h30, 5 h30, 10 h and 23 h30 reaction time.

The ratio increased from 1 h to 1 h45, but did not change between 1 h45 and 3 h. More GSC-ONH$_2$ re-agent was thus added (32 µl, 267 µg) at 4 h reaction time. Likewise, more re-agent was added after 10 h reaction time (0.9 mg) and the mixture was left at ambient temperature for a total of 23 h30.

The reaction mixture was purified on a SUPERDEX 200 10/300 GL (GE Healthcare) column using a Micro Äkta system (GE Health care). The eluent was 20 mM imidazole buffer pH 7.3, 10 mM CaCl$_2$, 0.02% TWEEN80, 1M glycerol, 0.5 M NaCl, with a flow of 0.4 ml/min, with fraction volume of 0.5 ml. Detection was at 210 and 272 nm. The relevant fractions were pooled, upconcentrated by ultra filtration on Millipore Amicon Ultra cut off 5 kD and used as such in next step. The concentration of the final product was estimated to be 0.27 mM (by comparison of a CMP (Sigma C1006) standard curve at 272 nm).

Example 10

Preparation of N-PSA(45 kD) (O)-PEG(40 kD) N8 Glycan by Sialyltransferase ST3Gal-III Catalyzed Reaction of (N-Asialo) (O)-PEG(40 kD) N8 with GSC-ON=PSA(45 kD)

1st Step:
(O)-PEG40 kD (N)-asialo N8:
The compound was synthesized according to the procedure described in Patent WO2009/108806 A1.
2nd step:
ST3Gal-III Catalyzed PSAylation of (N)-asialo (O)-PEG(40 kD) (N)-asialo N8 with GSC-ON=PSA(45 kD):
Solutions:
Reaction buffer: 20 mM imidazole buffer pH 7.3, 10 mM CaCl$_2$, 0.02% TWEEN 80, 1 M glycerol, 0.5M NaCl.
asialo-[O]-PEG40 kD-N8: 2.78 mg/ml
GSC-ON=PSA(45 kD 0.27 mM in reaction buffer
ST3Gal-III: (rat enzyme): MBP—SBP-ST3Gal III: 1 mg/ml
Procedure:
To the (N) asialo (O)-PEG40 kD-N8 solution (325 µl, 0.9 mg protein, 5.13 nmoles) was added the GSC-ON=PSA(45 kD) solution (190 µl, 51.3 nmoles, 2.3 mg, 10 equiv). The reaction was started by addition of the enzyme (116.3 µl, 116.3 µg). The reaction mixture was incubated at 32° C. for 17 h.

The product was capped by addition of a solution of NAN-CMP (1.2 mg) in 15 µl reaction buffer. The reaction mixture was incubated for 1 h at 32° C.

Work-Up and Purification:

The reaction mixture was diluted to 16 ml with 20 mM imidazol buffer pH 7.3, 10 mM $CaCl_2$, 1M glycerol, 0.02% TWEEN 80, 25 mM NaCl before purification by ion exchange on MonoQ 5/50 GL (GE Healthcare). The buffers used were: buffer A: 20 mM imidazole buffer pH 7.4 containing 10 mM $CaCl_2$, 1M glycerol, 0.02% TWEEN 80 (no NaCl), and buffer B: 20 mM imidazole buffer pH 7.4 containing 10 mM $CaCl_2$, 1 M glycerol, 0.02% TWEEN 80, 1 M NaCl.

The flow was 0.7 ml/min. The column was equilibrated for 20 CV. The elution profile was as follows: 0% B over 3 CV, 0-20% B over 5 CV, 20% B over 15 CV, 20 to 100% B over 15 CV, 100% B over 10 CV. The UV detection was at 280 nm. The fractionation was run at ambient temperature. The enzyme is eluted first, the product elutes later as a peak with a small shoulder. The fractions corresponding to the major peak were pooled and further purified and buffer exchanged on the size exclusion column SUPERDEX 200 10×300 GL (GE Healthcare), using a buffer containing 1.5 g/l L-Histidine, 3 g/l Sucrose, 18 g/l NaCl, 0.1 g/l TWEEN 80; 0.25 g/l $CaCl_2$, $2H_2O$, pH 7.3 as the eluent. The flow was 0.5 ml/min. The UV detection was at 280 nm. The product eluted as a major peak, followed by a minor peak, with base line separation between the peaks. The fraction corresponding to the major peak were pooled and upconcentrated by ultra-filtration on Millipore Amicon Ultra, 50 kD cut off. The protein recovery was 52%.

Product Characterization:

SDS PAGE Analysis:

The recovered product was run on a 7% Tris acetate SDS gel (150V, 1 h10) (Invitrogen) under reducing conditions, using Coomassie blue staining. The protein standard was the HiMark unstained HMW Protein Standard from Invitrogen.

With (O)-PEG (40 kD)-N8, the pegylated heavy chain band appeared at about 240 kD. After PSAylation, a band at higher MW appeared at about 290 kD. In addition, a wide and diffuse band (assumed to correspond to the PSAylated light chain) appeared at between 120 and 160 kD.

A very faint band corresponding to the molecular weight of the heavy chain of FVIII could be detected, and traces of a band corresponding to the light chain of FVIII could be seen.

Analysis on HPLC:

The analysis was run on a reverse phase Daiso 300 Å, 250×2.1, 5μ column. The eluents were: A: $H_2O$/TFA 0.1%, and B: $H_2O$/ACN/TFA (80:20:0.09%), the flow 0.25 ml/min, and the temperature of the column oven 40° C. The gradient was from 35% to 84% over 30 min. The HPLC was equipped with two detectors: a DAD detector (214 nm). The retention times of the heavy chain and light chain of the product were as indicated in the table below. The retention times of the heavy chain and light chain of N8 and of the intermediate (O)-PEG (40 kD)-N8 are indicated for comparison:

| | Sample | | |
|---|---|---|---|
| Rt | N8 | (O)-PEG(40 kD)-(N)-asialo N8 | (N)-PSA (45 kD)-(O)-PEG (40 kD)-N8 |
| Rt LC | 25.50 min | 25.46 min | 25.49 min |
| Rt HC | 29.95 min | 29.47 min | 29.38 min |

The same general profile is obtained for (N)-PSA (45 kD)-(O)-PEG (40 kD)-N8 as for [(N)-PSA (20 kD)-(O)-PEG (40 kD) N8 (cf example 6), i.e., the more polar final product (N)-PSA (45 kD)-(O)-PEG (40 kD) N8], shows retention times of the heavy and light chains that are shorter than the retention times for the HC and LC of the starting and intermediate compounds as expected. Activity:

The activity of the final product was measured in the chromogenic assay CoA test SP FVIII from Chromogenix according to the manufacturer instructions: compared to the starting N8, about 55% activity was recovered.

Example 11

Synthesis of N8 Conjugates of the Type (O)-PSA (N)-PSA-N8

General Description:

N8 was desialylated (reaction catalyzed by the sialidase from *Arthrobacter ureafaciens*) to give the (O)-asialo (N)-asialo N8. PSA was transferred onto the (O)-asialo glycan by the ST3Gal-I catalyzed reaction of GSC-ON=PSA (examples 5 or 9) with (O)-asialo (N)-asialo N8. After purification by ion exchange, the GSC-ON=PSA reagent was used as the donor in the ST3Gal-III catalyzed polysialylation of N-asialo (O)-PEG40 N8. Finally, any remaining unreacted galactose moiety was capped by adding NAN-CMP to the reaction mixture.

A detailed description of the synthesis of the conjugate of this type is given below:

$1^{st}$ Step: Preparation of (O)-PSA820 kD) (N)-Asialo N8 by Desialvlation of N8 and ST3Gal-I Catalyzed Transfer of PSA onto (O)-Asialo Glycans of N8 (One Pot Reactions):

Solutions:

Reaction buffer: 20 mM imidazole buffer pH7.3, 10 mM $CaCl_2$, 0.02% TWEEN 80, 1 M glycerol, 0.5 M NaCl.

N8: 5.7 mg/ml in reaction buffer (8650 U/mg)

Sialidase: from *Arthrobacter ureafaciens* 0.4 mg/ml, 242 U/mg

GSC-ON=PSA(20 kD): 25 mg/ml in (3 g/l Sucrose, 1.5 g/l L-Histidine, 18 g/l NaCl, 0.1 g/l TWEEN 80; 0.25 g/l $CaCl_2$; pH 7.3).

His-ST3Gal-I; AA46-343; 2.5 mg/ml in (50 mM Tris pH8, 100 mM NaCl)

Procedure:

To a solution of N8 in reaction buffer (1.5 mg, 8.5 nmoles, 263 μl) was added a solution of the *A. ureafaciens* sialidase (7 μl, 678 mU, 1.5 Wml final) and a solution of the ST3Gal-I enzyme (108 μl, 0.27 mg). A solution of GSC-ON=PSA(20 kD) was added (68 μl, 1.7 mg, about 85 nmoles, about 10 equiv). The reaction mixture was incubated at 23° C. for 24 h.

Work-Up and Purification:

The reaction mixture was diluted twenty times with a buffer containing (20 mM imidazole buffer pH 7.3, 10 mM $CaCl_2$, 0.02% TWEEN 80, 1M glycerol), and purified on an ion exchange column (MonoQ 5/50 GL, GE Healthcare). The elution buffers were: buffer A: 20 mM imidazole buffer pH 7.3, 10 mM $CaCl_2$, 0.02% TWEEN 80, 1M glycerol, and buffer B: buffer A added 1.5 M NaCl. The flow was 0.35 ml/min. The purification was run at 15° C. The detection was done by UV, 280 nm. The elution was as follows: from 0 to 20% B over 5 CV, from 20 to 100% B over 25CV, 100% B for 5 CV. 1 ml fractions were collected in a 96 deep well plate.

Relevant fractions were analyzed by SDS PAGE (7% Tris acetate SDS gel (150V, 1 h10) (Invitrogen) under reducing conditions, using silver staining. The protein standard was the HiMark unstained HMW Protein Standard from Invitrogen). Fractions corresponding to the main peak contain a mixture of N8 (about 35% of N8 is not O-glycosylated (Thim et al., Haemophilia (2010), 16(Suppl 5), 194) and (O)-PSAylated N8. Traces of the sialidase or the ST3Gal-I enzyme could not be detected.

Fractions corresponding to the main peak were pooled and upconcentrated by ultrafiltration (Millipore Amicon Ultra, cut off 50 kD), giving a solution with a protein concentration of 5.5 mg/ml according to reverse phase HPLC analysis (for HPLC method details: see example 10). The protein recovery was about 79%.

2nd Step: Synthesis of (O)-PSA(20 kD) (N)-PSA(20 kD) N8 by ST3Gal-III Catalyzed Transfer of PSA onto (N)-Asialo Glycans of (O)-PSA(20 kD) (N)-Asialo N8:

Solutions:
  Mixture of (O)-PSA(20 kD)-(N)-asialo N8 and N8 (from step 1): 5.5 mg protein/ml
  GSC-ON=PSA(20 kD): 25 mg/ml in (3 g/l Sucrose, 1.5 g/l L-Histidine, 18 g/l NaCl, 0.1 g/l TWEEN 80; 0.25 g/l $CaCl_2$; pH7.3).
  ST3Gal-III: (MBP-SBD-ST3Gal-III) 0.33 mg/ml in (14 mM HEPESpH7, 140 mM NaCl, 50% glycerol). 0.54 U/ml. Upconcentrated (about 15 times) by ultrafiltration on Millipore Biomax cut off 5 kD.
  NAN-CMP: 50 mg/ml in 20 mM imidazole buffer pH 7.3, 10 mM $CaCl_2$, 0.02% TWEEN 80, 1 M glycerol.

Procedure:
To the mixture of (O)-PSA(20 kD)-(N)-asialo N8 and N8 obtained in the first step (210μl, 6.4 nmoles) is added a solution of GSC-ON=PSA(20 kD) (26 μl, 32 nmoles). The reaction was started by the addition of the ST3Gal-III enzyme solution (40 μl, 324 mU, 198 μg). The reaction mixture was incubated at 32° C. After 3 h reaction time, a new portion of the GSC-ON=PSA(20 kD) solution was added (20 μl, 25 nmoles) The reaction mixture was incubated for 21 h.

Capping:
To the reaction mixture above was added a solution of NAN-CMP (10 μl, 0.5 mg). The mixture was incubated at 32° C. for 2 h.

Work-Up and Purification:
The reaction mixture was diluted twenty times in 20 mM imidazole buffer pH 7.4, 10 mM $CaCl_2$, 0.02% TWEEN 80, 1 M glycerol.

It was then purified on an IEX membrane (Sartorius Vivapure Q Mini M) according to the manufacturer instructions, using buffer A (20 mM imidazole buffer pH 7.4, 10 mM $CaCl_2$, 0.02% TWEEN 80, 1 M glycerol) as the washing buffer and buffer B (buffer A added NaCl to 1 M concentration) as the elution buffer.

The eluted product was upconcentrated by ultra filtration (Millipore Amicon Ultra device, cut-off 50 kD) before purification and buffer shift on a size exclusion column (SUPERDEX 200 10/30 GL, GE Healthcare). The buffer contained sucrose (3 g/l), L-Histidine (1.5 g/l), NaCl (18 g/l), TWEEN 80 (0.1 g/l), and $CaCl_2$ (0.25 g/l) pH 7.3. The flow was 0.4 ml/min, the detection was by UV at 280 nm. 0.5 ml fractions were collected.

Remaining ST3Gal-III (probably aggregates) appeared as a shoulder eluting before the main peak. Fractions corresponding to the main peak (and not containing St3Gal-III) were pooled. and quantified by HPLC (see example 10 for HPLC method details). The overall protein recovery (starting from N8) was 28%.

Product Characterization:
SDS PAGE Analysis:
The recovered product was run on a 7% Tris-acetate SDS gel (150V, 1 h10) (Invitrogen) under reducing conditions, using Coomassie blue staining. The protein standard was the HiMark unstained HMW Protein Standard from Invitrogen.

A very wide and diffuse band appeared between 97 kD and 160 kD: this is assumed to correspond to the PSAylated heavy and light chains. Traces of underivatized heavy chain and the light chain are detectable. The band appearing between 240 and 280 kD was assumed to correspond to the PSAylated single chain N8.

Analysis on HPLC:
The analysis was run as indicated in example 10.
The retention times of the heavy chain and light chain of the product were as indicated in the table below. The retention times of the heavy chain and light chain of N8 are indicated for comparison:

|  | Sample | |
| --- | --- | --- |
| Rt | N8 | (O)-PSA(20 kD) N-PSA(20 kD) N8 |
| Rt LC | 25.44 min | 25.39 min |
| Rt HC | 29.89 min | 29.61 min |

Thus, the PSAylated HC retention time decreases (and the peak appears wider) as expected for a more polar protein. The effect is less obvious for the PSAylated light chain, also reflecting the fact that only two potential derivatization sites are available, while three are available for the heavy chain ((O)- and (N)-glycans of the HC).

Activity:
The activity of the final product was measured in the chromogenic assay CoA test SP FVIII from Chromogenix: compared to the starting FVIII: about 55% activity was recovered.

Examples 12 and 13

Synthesis of N8 Conjugates of the Type (N)-PSA-N8

General Description:
N8 was desialylated using the sialidase from *Clostridium perfringens* to give the (N)-asialo N8. The GSC-ON=PSA reagent was used as the donor in the ST3Gal-III catalyzed polysialylation of N-asialo (O)-PEG40 N8. Finally, any remaining unreacted galactose moiety was capped by adding NAN-CMP to the reaction mixture. A detailed description of the synthesis of the conjugates of this type is given below:

Example 12

Synthesis of (N)-PSA(45 kD) N8

1st Step: Desialylation of N8 by *C. perfringens* Sialidase:
Solutions:
  Reaction buffer: 20 mM imidazole buffer pH 7.3, 10 mM $CaCl_2$, 0.02% TWEEN 80, 1 M glycerol, 0.5 M NaCl.
  sialidase: 0.3 mg/ml 200 U/ml
  N8: 5.7 mg/ml in reaction buffer Procedure:
To the N8 solution (350 μl, 2 mg) was added the reaction buffer (350 μl) and the enzyme solution (20 μl, 4 U). The mixture was incubated for 45 min at 23° C.

Work-Up and Purification:
The reaction mixture was diluted ten times with (20 mM imidazole buffer pH 7.3, 10 mM $CaCl_2$, 0.02% TWEEN 80, 1 M glycerol, 0.15 M NaCl). The solution obtained was purified on an anion exchange column (MonoQ 5/50 GL, GE Healthcare) on an Akta Purifier (GE Healthcare). The buffers used were: buffer A: 20 mM imidazole buffer pH 7.3, 10 mM $CaCl_2$, 0.02% TWEEN 80, 1 M glycerol, 25 mM NaCl, and buffer B: buffer A with 1M NaCl. The flow was: 0.5 ml/min, the detection was by UV, 280 nm. The elution was done as follows: from 0 to 20% B over 5 CV, 20% B over 10 CV, 100%

B over 10 CV. The eluate was collected in 0.5 ml fractions in the last gradient step. The protein recovery was 45%.

2nd Step: Synthesis of (N)-PSA(20 kD) N8 by ST3Gal-III Catalyzed Transfer of PSA onto (N)-asialo N8:

Re-agents:
Reaction buffer: 20 mM imidazole buffer pH 7.3, 10 mM CaCl$_2$, 0.02% TWEEN 80, 1 M glycerol, 0.5 M NaCl.
[N]-asialo-N8: 2.39 mg/ml in 20 mM imidazole buffer pH 7.3, 10 mM CaCl$_2$, 0.02% TWEEN80, 1 M glycerol, 0.25 M NaCl
GSC-ON=PSA(45 kD): about 0.27 mM in reaction buffer (12.1 mg/ml)
ST3Gal III: (rat enzyme): MBP—SBP-ST3Gal III, 1 mg/ml, 1.2 U/mg Procedure:
To the solution of [N]-asialo-N8 (364 µl, 0.87 mg protein) was added the solution of GSC-ON=PSA(45 kD) (183 µl, 2.22 mg). The reaction was started by addition of the enzyme (122 µl, 122 µg, 146 mU). The mixture was incubated overnight at 32° C.

Capping:
A solution of NAN-CMP (1.3 mg in 15 µl reaction buffer) was added and the resulting mixture incubated for 1 h at 32° C.

Work-Up and Purification:
The reaction mixture was diluted ten times with 20 mM imidazole buffer pH 7.3, 10 mM CaCl$_2$, 0.02% TWEEN 80, 1 M glycerol, 25 mM NaCl, and purified by anion exchange (MonoQ 5/50 GL, GE Healthcare) on an Äkta Purifier system (GE Healthcare). The buffers used were: buffer A: 20 mM imidazole buffer pH 7.3, 10 mM CaCl$_2$, 0.02% TWEEN 80, 1 M glycerol, 25 mM NaCl, and buffer B: buffer A with 1 M NaCl. The flow was: 0.7 ml/min, the detection was by UV, 280 nm. The purification was run at 15° C. The elution was done as follows: from 0 to 20% B over 5 CV, 20% B over 15 CV, 20 to 100% B over 15 CV, 100% B over 10 CV. The eluate was collected in 0.5 ml fractions. The protein recovery was 32%.

Characterization of the Product:

SDS PAGE Analysis:
The recovered product was run on a 7% Tris-acetate SDS gel (150V, 1 h10) (Invitrogen) under reducing conditions, using Coomassie blue staining. The protein standard was the HiMark unstained HMW Protein Standard from Invitrogen.

A rather wide and diffuse band appeared between about 125 and 165 kD: this is assumed to correspond to the PSAylated heavy and light chains. Traces of underivatized heavy chain and light chain are detectable.

Reverse Phase HPLC Analysis:
The analysis was run as indicated in example 10.
The retention times of the heavy chain and light chain of the product were as indicated in the table below. The retention times of the heavy chain and light chain of N8 are indicated for comparison:

|  | Sample | |
| --- | --- | --- |
| Rt | N8 | (N)PSA(45 kD) N8 |
| Rt LC | 25.46 min | 25.43 min |
| Rt HC | 29.92 min | 29.72 min |

Thus, the PSAylated HC retention time decreases (and the peak appears wider) as expected for a more polar protein. The effect is almost negligible on the retention time of the PSAylated light chain.

Activity:
The activity of the final product was measured in the chromogenic assay CoA test SP FVIII from Chromogenix: compared to the starting FVIII: about 60% activity was recovered.

Example 13

Synthesis of (N)-PSA(20 kD) N8

The synthesis was performed similarly to the synthesis of (N)-PSA(45 kD) N8. The protein recovery was 39%.

Characterization:
SDS-PAGE Analysis: Performed as in Example 12.
A very wide and diffuse band appeared between about 97 and 160 kD: this is assumed to correspond to the PSAylated heavy and light chains. Bands corresponding to traces of underivatized heavy chain (traces) and light chain (sizable amounts) are detectable.

Reverse Phase HPLC Analysis:
The analysis was run on a reverse phase Daiso 300 Å, 250×24, 5µ column. The eluents were: A: H$_2$O/TFA 0.1%, and B: H$_2$O/ACN/TFA (80:20:0.09%), the flow was 1 ml/min, and the temperature of the column oven 40° C. The gradient was from 35% to 84% over 30 min. The HPLC was equipped with two detectors: a DAD detector (214 nm). The retention times of the heavy chain and light chain of the product were as indicated in the table below. The retention times of the heavy chain and light chain of N8 are indicated for comparison:

|  | Sample | |
| --- | --- | --- |
| Rt | N8 | (N)-PSA(20 kD) N8 |
| Rt LC | 17.48 min | 17.49 min |
| Rt HC | 21.92 min | 21.77 min |

Thus, as for the (N)-PSA(45 kD) N8 compound, the PSAylated HC retention time decreases (and the peak appears wider) as expected for a more polar protein. The effect is negligible on the retention time of the PSAylated light chain.

Activity:
The activity of the final product was measured in the chromogenic assay CoA test SP FVIII from Chromogenix: compared to the starting FVIII: about 88% activity was recovered.

3. PK studies in FVIII KO mice: Comparison of half-lives of various N8 glyco-PEG/PSA derivatives.

Example 14

Pharmacokinetic Characterisation of N8 Glyco-Conjugates

The pharmacokinetics of rFVIII variants were evaluated in FVIII-deficient mice (FVIII exon 16 knock out (KO) mice with C57B1/6 background. The FVIII-KO mice had no detectable FVIII:C. A mixture of male and female (approximately 1:1) with an approximate weight of 25 grams and age range of 16-28 weeks were used. The mice received a single i.v. injection of rFVIII (280 IU/kg) in the tail vein. Blood was taken from the orbital plexus at time points up to 64 hours after dosing using non-coated capillary glass tubes. Three samples were taken from each mouse, and 2 to 4 samples were collected at each time point. Blood was immediately stabilized with sodium citrate and diluted in four volumes FVIII Coatest SP buffer (50 mM Tris, 150 mM NaCl, 1% BSA, pH 7.3, with preservative) before 5 min centrifugation at 4000×g.

Plasma obtained from diluted blood was frozen on dry ice and kept at −80° C. The FVIII:C was determined in a chromogenic assay using Coatest SP reagents (Chromogenix) according to the manufacturer instructions. Pharmacokinetic analysis was carried out by non-compartmental methods (NCA) using WinNonlin Pro software. The table below shows estimates for half-lifves (T1/2).

| Compound # | Compound | Chromogenic activity (% N8) | T½ (h) | T½ prolongation |
|---|---|---|---|---|
| A | (N)-PSA(20 kD) N8 | 88 | 11.0 | x1.6 |
| B | (N)-PSA(45 kD) N8 | 60 | 15.0 | x2.2 |
| C | (O)-PEG(40 kD) N8 | >90 | 14.0* | x2.0 |
| D | (O)-PSA(20 kD) (N)-PSA(20 kD) N8 | 92% | 12.6 | x1.9 |
| E | (O)-PEG40 kD) (N)-PEG(40 kD) N8 | n.d. | 13.0 | x1.9 |
| F | (O)-PEG40 kD) (N)-PSA(20 kD) N8 | 93 | 17.7 | x2.6 |
| G | (O)-PEG40 kD) (N)-PSA(45 kD) N8 | 55 | 19.5* | X2.9 |
| H | N8 | 100 | 6.8* | x1.0 |

*when the same compound was tested several times, the value of the half-life indicated in the table is the average of the half-lives obtained for each experiment.

The compound C, where the (branched) PEG40 kD moiety is linked to the (0)-glycan, has a half-life of 14 h, i.e., the half-life of N8 is prolonged by a factor 2. Further conjugation of polymers on the N-glycans have markedly different effects on the half-life of the resulting compounds:
  conjugation of another PEG40 kD moiety does not have any effect on the resulting compound E ($T_{1/2}$=13 h)
  while the conjugation of (linear) PSA (of either 20 or 45 kD molecular weight) does have a marked effect on the resulting compounds: compounds F and G have half lives of respectively 17.7 h and 19.5 h, prolonging the haf-life of the original N8 molecule by a factor 2.6, respectively 2.9. (The last one at the expense of half of the activity, though.)

Likewise, N8 derivatized with PSA(20 kD) on both (O)- and (N)-glycans (compound D) shows a half-life which is identical to the half-life of the N8 derivatized with PEG(40 kD) on both (O)- and (N)-glycans (compound E): T1/2=12.6 h vs 13 h; this is only a modest improvement compared to the half-life of the N8 derivatized solely at the (N)-glycans (compound A) (T1/2=11 h). However, when PEG(40 kD) is present on O)-glycan instead of PSA(20 kD), the half-life of the resulting compound F ((O)-PEG40 kD) (N)-PSA(20 kD) N8) is markedly increased: 17.7 h vs. 12.6 h for compound D.

These results strongly suggest that the combination of PEG and PSA for glyco derivatization is superior to the use of only one polymer type.

These results are surprising: the branched PEG 40 kD was expected to have a prolonging effect due to its ability to cover the surface of the protein, thereby preventing access or make access more difficult for proteases to N8 surface or prevent/decrease binding of N8 to clearance receptors. As a branched polymer, it is expected to do so more effectively than a linear polymer (Veronese et al., J. Bioactive and Compatible Polymers (1997)12, 196). If only the steric parameters are at play, one would have expected an even better protection of the N8 surface by a branched polymer than by a linear polymer, and a fortiori a linear polymer of half the molecular way of the branched poymer. Both polymers are highly hydrated, their structures are similar (mostly random coil).

Example 15

Preparation of Sialyltransferase Substrate (4-formylbenzoyl)glycyl Sialic Acid Cytosine 5'-monophosphate Ester (Aldehyde-GSC, J-1)

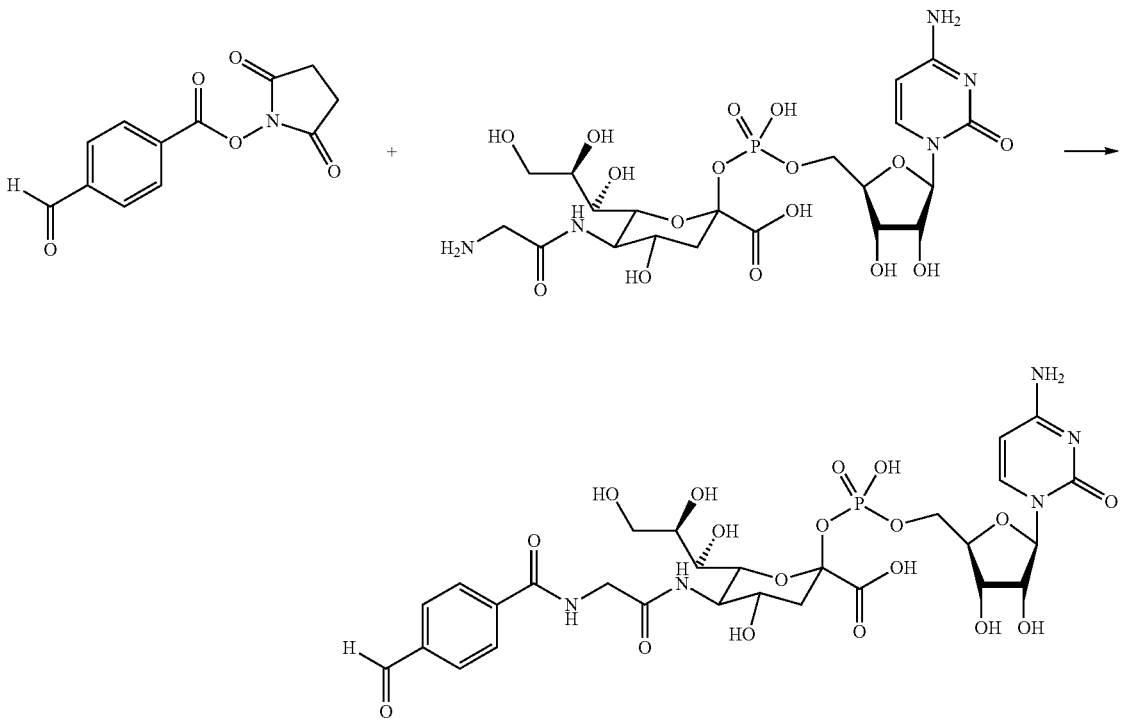

J-1

Succinimidyl 4-formylbenzoate (100 mg, 0.41 mmol) was dissolved in THF (3 ml) and TRIS buffer (100 mM, pH 8.5, 4 ml) was added. Glycyl sialic acid cytidine 5'-monophosphate ester (GSC, 250 mg, 0.34 mmol) was weighed out and added to the solution of NHS-ester and allowed to react at rt. for a period of 2.5 h. The reaction mixture was diluted to 4 ml with 15 ml 10 mM ammonium bicarbonate buffer and purified by RP HPLC. System: Waters 2545 gradient controller, 2489 UV detector. Column: C18, Ø 2 cm. Gradient 0->30% $CH_3CN$ with 10 mM ammonium bicarbonate. Relevant fractions were identified by LCMS and freeze-dried. The product was then re-purified by RP-HPLC. Yield: 62 mg. The product was identified by LCMS.

Using the above protocol, a sialyl transferase substrate carrying a chemoselective aldehyde functional group was prepared.

Example 16

Preparation of Alkoxylamine Functionalised Hydroxyethyl Starch (HES-$ONH_2$)

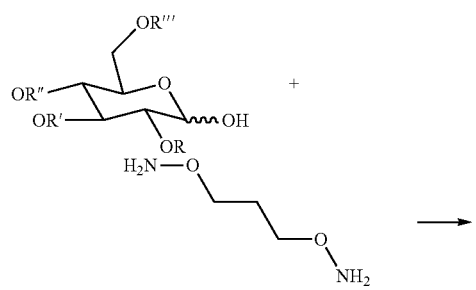

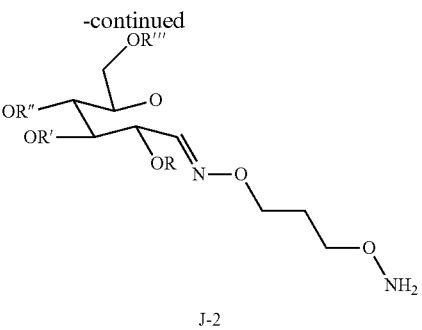

J-2

Where R may be either H, ——$CH_2CH_2OH$, or further branching (starch)

HES 200/0.5 infusion liquid ("HyperHAES", Fresenius Kabi, 80 ml, 60 g/l, 4.8 g, 24 μmol) was mixed with a solution of 1,3-bisaminoxypropane.2HCl (1.8 g, 10.2 mmol, 425 eq.), bringing pH to 1.66. The mixture was stirred at ambient temperature overnight. An amount of 20 ml of the reaction mixture was diluted with 250 ml of water. The diluted sample was purified by tangential filtration against 5 l of water using a Vivaflow 50 system (Sartorius, 10 kDa MWCO PES membrane, pressure after pump approx. 2.5, waste: 7 ml/min). Finally, it was concentrated to 50 ml and the system was flushed with 50 ml water. After freeze drying, 690 mg of product was obtained.

In a similar fashion, HES-$ONH_2$ was prepared from HES 130/0.4 starting from Voluven® infusion liquid (Fresenius Kabi)

Using the above protocol, a hydroxyethyl starch with a chemoselective alkoxylamine functional group was prepared.

Example 17

Coupling of Aldehyde-GSC (J-1) with Alkoxylamine Funtionalised Hydroxyethyl Starch HES-$ONH_2$ (J-2) to Obtain a HES-GSC Conjugate (J-3)

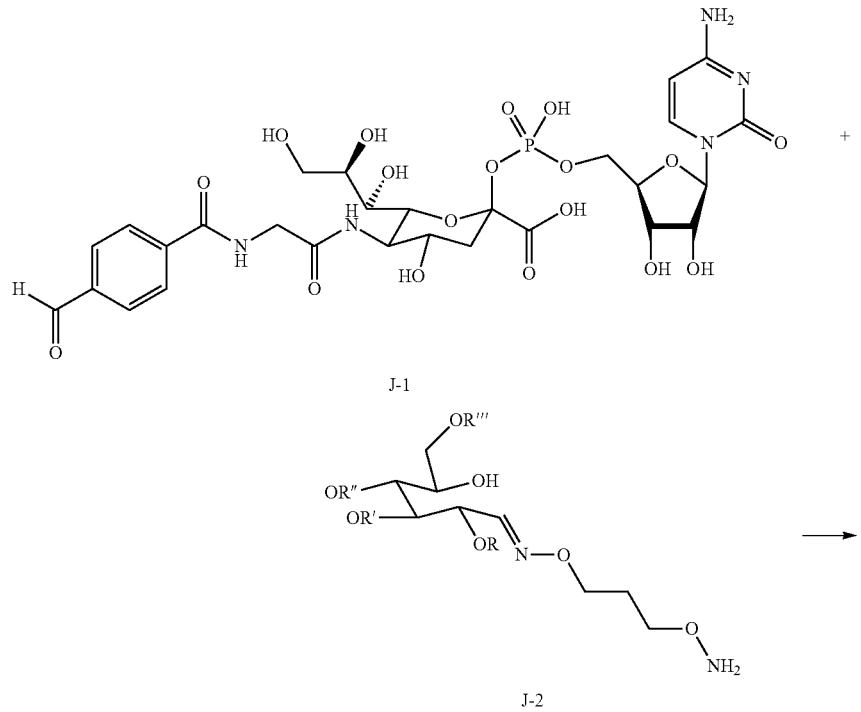

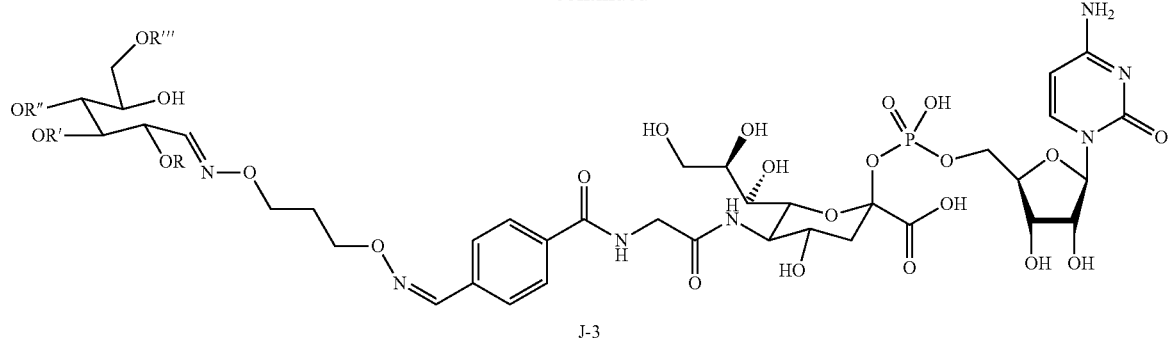

J-3

The HES-ONH$_2$ (J-2) (100 mg, 0.5 μmol) was dissolved in 1000 ul of PBS-buffer pH 7.4 and the aldehyde-GSC (J–1) (31 mg, 41 μmol) was added. The reaction was allowed to proceed at r.t. for a period of 22 h after which the reaction mixture was diluted with 100 ml with PBS-Buffer pH 7.3. The diluted sample was purified by tangential filtration against 4 l of PBS buffer using a Vivaflow 50 system (Sartorius, 10 kDa MWCO RC membrane). The product was obtained in 100 ml buffer containing 140 mg HES-GSC. The product was characterised by SEC (Column: BioSep-SEC-S3000, 5 μm, 290 Å column 300×7.8 mm, buffer: PBS-buffer pH 7.3, flow: 1 ml/min) with detection at 276 nm for cytidine. Only high molecular weight cytidine-derivatives were detected in the product by this method, and it was concluded that the product was essentially free of the starting material aldehyde-GSC.

Using the above protocol, a sialyl transferase substrate was prepared which is useful for the attachment of hydroxyethyl starch to de-sialylated glycans of glycoproteins.

Example 18

Modification of Wt B-Domain Deleted Human FVIII (N8) with HES on the O-Glycan Using HES-GSC Substrate J-3 and ST3Gal-I to Obtain a HES-FVIII Conjugate HES-GSC (10 eq., 45 mg, 50 ml, 1 mg/ml in PBS-buffer) was concentrated and buffer exchanged to 20 mM imidazol, 10 mM CaCl$_2$, 0.02% TWEEN 80, 1 M glycerol, pH 7.3, 1 M NaCl using Amicon Ultra ultra-filtration vial. Final volume 2.2 ml. The HES-GSC re-agent was mixed with N8 (4 mg, 22 nmol, 5.7 mg/ml), sialidase A. Urifaciens (40 μl, 130 U/ml, 0.43 mg/ml, 5.2 U), and His-ST3Gal-I (400 μl, 2.5 mg/ml) and incubated at 32° C. After a period of 22 h, SDS PAGE analysis showed product formation as a smeared band migrating at higher MW than both HC and LC FVIII bands. The reaction mixture was diluted with approx. 50 ml of buffer 20 mM imidazol, 10 mM CaCl$_2$, 0.02% TWEEN 80, 1 M glycerol, pH 7.3, 25 mM NaCl to lower the conductivity and purified by anion exchange chromatography. Column: MonoQ 5/50 GL, start buffer: 20 mM imidazol, 10 mM CaCl$_2$, 0.02% TWEEN 80, 1 M glycerol, pH 7.3, 25 mM NaCl, elution buffer: 20 mM imidazol, 10 mM CaCl$_2$, 0.02% TWEEN 80, 1 M glycerol, pH 7.3, 1 M NaCl. Relevant fractions containing the desired product was identified from SDS PAGE analysis as having three main bands: an intact LC, an HC band with very reduced intensity, and a smeared band of high MW representing HES conjugated to HC. The isolated pooled fractions contained 1.11 mg product (based on FVIII A280, 0.275 mg/ml). The pooled fractions (4 ml) were mixed with 100 μl of CMP-NAN (25 mg/ml in buffer 20 mM imidazol, 10 mM CaCl$_2$, 0.02% TWEEN 80, 1 M glycerol, pH 7.3, 25 mM NaCl) and ST3Gal-III (100 μl, 1.2 U/ml) and incubated for 1 hour at 32° C. The reaction mixture was then diluted with a buffer 20 mM imidazol, 10 mM CaCl$_2$, 0.02% TWEEN 80, 1 M glycerol, pH 7.3, 25 mM NaCl, and loaded to a Vivapure Q, Maxi M spin filter (Sartorius). The filter was washed with 2×15 ml 20 mM imidazol, 10 mM CaCl$_2$, 0.02% TWEEN 80, 1 M glycerol, pH 7.3, 25 mM NaCl and eluted using first 2×15 ml 20 mM imidazol, 10 mM CaCl$_2$, 0.02% TWEEN 80, 1 M glycerol, pH 7.3, 200 mM NaCl (to remove ST3Gal-III) and then 3×0.5 ml 20 mM imidazol, 10 mM CaCl$_2$, 0.02% TWEEN 80, 1 M glycerol, pH 7.3, 1 M NaCl to elute the product. The two first fractions contained the desired product, with 800 μg and 110 μg, respectively (based on FVIII A280). These two fractions were purified separately by SEC (column SUPERDEX 200 10/300 GL, buffer: histidine (1.5 mg/ml), CaCl$_2$ (0.25 mg/ml), TWEEN 80 (0.1 mg/ml), NaCl (18 mg/ml), sucrose (3 mg/ml)) resulting in recovery of 218 μg and 66 μg, respectively (based on FVIII A280). Protein concentration determination by HPLC gave yields of 130 μg and 40 μg, respectively (based on FVIII absorption at 280 nm).

Using the above protocol, a HES-FVIII conjugate was prepared in which the HES was coupled to FVIII via the O-glycan of the B-domain linker. This conjugation strategy lead to a site-selectively HESylated FVIII-molecule. Moreover, the sialyltransferase mediated conjugation is mild.

Example 19

Modification of Wt B-Domain Deleted Human FVIII (N8) with HES on the O-Glycan Using HES-GSC Substrate J-3 and ST3Gal-I, and PEG on the N-Glycans Using PEG-GSC and ST3Gal-III to Obtain a Simultaneous PEGylated and HESylated FVIII Conjugate The conjugate prepared according to Example 18 is treated with an immobilised sialidase, PEG-GSC and ST3Gal-III in a one-pot reaction in an aqueous buffer. After complete reaction, the sialidase is removed by filtration and a large excess of CMP-NAN is added to the reaction mixture to block any terminal galactose. After complete reaction, the conjugate is purified by anion-exchange and SEC chromatography to separate the product from the ST3Gal-III and sialyltransferase substrates.

Using this protocol a FVIII conjugated with HES and PEG on O- and N-glycans, respectively, are produced.

Example 20

Modification of Wt B-Domain Deleted Human FVIII (N8) with HES on the N-Glycans Using HES-GSC Substrate J-3 and ST3Gal-111, and PEG on the O-Glycans Using PEG-GSC and ST3Gal-I to Obtain a Simultaneous PEGylated and HESylated FVIII Conjugate An O-glycan PEGylated FVIII is prepared according to WO 2009/108806 A1. This conjugate is treated with an immobilised sialidase, HES-GSC J-3 of Example 17 and ST3Gal-III in a one-pot reaction in an aqueous buffer. After complete reaction, the sialidase is removed by filtration and a large excess of CMP-NAN is added to the reaction mixture to block any terminal galactose. After complete reaction, the conjugate is purified by anion-exchange and SEC chromatography to separate the product from the ST3Gal-III and sialyltransferase substrates.

Using this protocol a FVIII conjugated with HES and PEG on N- and O-glycans, respectively, are produced.

Example 21

Preparation of Sulfated PSA

The preparation is done according to published procedures (for example Kunou et al., Biomacromolecules, (2000), 1, 451 and references cited therein). The starting material is either a PSA of molecular weight about 20 kD, or a PSA of molecular weight about 45 kD, obtained as described in examples 3 and 7.

Briefly, the sodium salt of PSA is changed to the tri-n-butylammonium salt in order to increase its solubility in organic solvents. This is done on resin ion exchange (Amberlite IR120B, H+ type). Sulfation of the lyophilized tributyl ammonium salt is performed in anhydrous DMF under inert atmosphere at 0° C., using SO3-pyridine complex as sulfation reagent. The reaction is terminated by addition of water and adjustment of pH to 9. The product is recovered by adding the reaction mixture dropwise to a large volume of acetone. The product is recovered by centrifugation of the resulting precipitate. The product is further purified by gel filtration and the eluate is lyophilized.

Example 22

Sodium Periodate Oxidation of Sulfated PSA

The periodate oxidation is performed in the same way as in example 8, starting with the sulphated PSA obtained in example 21.

Example 23

Coupling of Sodium Periodate Oxidized Sulfated PSA to GSC-ONH$_2$ to Yield the sialyltransferase ST3Gal-III Substrate GSC-ON=Sulfated PSA The coupling is done according to example 9, using GSC-ONH$_2$ from example 2 and the oxidized sulfated PSA from example 22 as starting compounds.

Example 24

Preparation of (N)-Sulfated PSA-(O)-PEG (40 kD) N8 by Sialyltransferase ST3Gal-III catalyzed reaction of (N)-asialo (O)-PEG(40 kD) N8 with GSC-ON=sulfated PSA The compound is prepared according to example 10, using (N)-asialo (O)-PEG(40 kD) N8 as acceptor and GSC-ON=sulfated PSA as donor in presence of ST3Gal-III.

---

The invention claimed is:

1. A Factor VIII (FVIII) variant comprising a FVIII molecule with a truncated B-domain, wherein the truncated B-domain is SEQ ID NO:2, wherein the FVIII variant is covalently heteroconjugated with: (1) at least one poly(ethylene glycol) (PEG) polymer via an O-linked oligosaccharide in the truncated B-domain; and (2) at least one poly(sialic acid) (PSA) polymer via an N-linked oligosaccharide.

2. The FVIII variant according to claim 1, further comprising two to four PSA polymers linked to one double-branched N-linked oligosaccharide in the A1 domain and one double-branched N-linked oligosaccharide in the A3 domain.

3. The FVIII variant according to claim 1, wherein said variant comprises one or two PSA polymers linked to one double-branched N-linked oligosaccharide in the A1 domain.

4. The FVIII variant according to claim 1, wherein said variant comprises one or two PSA polymers linked to one double-branched N-linked oligosaccharide in the A3 domain.

5. The FVIII variant according to claim 1, wherein the size of the PEG polymer is 30-50 kDa.

6. The FVIII variant according to claim 1, wherein the size of the PSA polymer is 20-50 kDa.

7. A method of making a FVIII variant according to claim 1, wherein said method comprises conjugating a FVIII molecule with at least one PEG polymer and at least one PSA polymer.

8. A pharmaceutical composition comprising a FVIII variant according to claim 1 and optionally one or more pharmaceutically acceptable excipients.

9. A method for treating hemophilia A comprising administering the FVIII variant according to claim 1 to a patient in need thereof.

* * * * *

SEQUENCE LISTING

<160> NUMBER OF SEQ ID NOS: 2

<210> SEQ ID NO 1
<211> LENGTH: 2332
<212> TYPE: PRT
<213> ORGANISM: homo sapiens

<400> SEQUENCE: 1

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
```

-continued

```
            115                 120                 125
Phe Pro Gly Gly Ser His Thr Tyr Val Trp Gln Val Leu Lys Glu Asn
        130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Arg Glu Gly Ser Leu Ala Lys Glu Lys Thr Gln Thr Leu
                180                 185                 190
His Lys Phe Ile Leu Leu Phe Ala Val Phe Asp Glu Gly Lys Ser Trp
                195                 200                 205
His Ser Glu Thr Lys Asn Ser Leu Met Gln Asp Arg Asp Ala Ala Ser
        210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
                260                 265                 270
Gly His Thr Phe Leu Val Arg Asn His Arg Gln Ala Ser Leu Glu Ile
                275                 280                 285
Ser Pro Ile Thr Phe Leu Thr Ala Gln Thr Leu Leu Met Asp Leu Gly
        290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Pro Gln Leu Arg
                325                 330                 335
Met Lys Asn Asn Glu Glu Ala Glu Asp Tyr Asp Asp Leu Thr Asp
                340                 345                 350
Ser Glu Met Asp Val Val Arg Phe Asp Asp Asn Ser Pro Ser Phe
                355                 360                 365
Ile Gln Ile Arg Ser Val Ala Lys Lys His Pro Lys Thr Trp Val His
        370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
                420                 425                 430
Asp Glu Thr Phe Lys Thr Arg Glu Ala Ile Gln His Glu Ser Gly Ile
        435                 440                 445
Leu Gly Pro Leu Leu Tyr Gly Glu Val Gly Asp Thr Leu Leu Ile Ile
        450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
                515                 520                 525
Leu Thr Arg Tyr Tyr Ser Ser Phe Val Asn Met Glu Arg Asp Leu Ala
        530                 535                 540
```

-continued

```
Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
                740                 745                 750

Gln Lys Gln Phe Asn Ala Thr Thr Ile Pro Glu Asn Asp Ile Glu Lys
            755                 760                 765

Thr Asp Pro Trp Phe Ala His Arg Thr Pro Met Pro Lys Ile Gln Asn
        770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
        850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
                900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Glu Asn Asn Asp
        930                 935                 940

Ser Lys Leu Leu Glu Ser Gly Leu Met Asn Ser Gln Glu Ser Ser Trp
945                 950                 955                 960
```

-continued

Gly Lys Asn Val Ser Ser Thr Glu Ser Gly Arg Leu Phe Lys Lys
                    965                 970                 975
Arg Ala His Gly Pro Ala Leu Leu Thr Lys Asp Asn Ala Leu Phe Lys
            980                 985                 990
Val Ser Ile Ser Leu Leu Lys Thr Asn Lys Thr Ser Asn Asn Ser Ala
        995                 1000                1005
Thr Asn Arg Lys Thr His Ile Asp Gly Pro Ser Leu Leu Ile Glu
    1010                1015                1020
Asn Ser Pro Ser Val Trp Gln Asn Ile Leu Glu Ser Asp Thr Glu
    1025                1030                1035
Phe Lys Lys Val Thr Pro Leu Ile His Asp Arg Met Leu Met Asp
    1040                1045                1050
Lys Asn Ala Thr Ala Leu Arg Leu Asn His Met Ser Asn Lys Thr
    1055                1060                1065
Thr Ser Ser Lys Asn Met Glu Met Val Gln Gln Lys Lys Glu Gly
    1070                1075                1080
Pro Ile Pro Pro Asp Ala Gln Asn Pro Asp Met Ser Phe Phe Lys
    1085                1090                1095
Met Leu Phe Leu Pro Glu Ser Ala Arg Trp Ile Gln Arg Thr His
    1100                1105                1110
Gly Lys Asn Ser Leu Asn Ser Gly Gln Gly Pro Ser Pro Lys Gln
    1115                1120                1125
Leu Val Ser Leu Gly Pro Glu Lys Ser Val Glu Gly Gln Asn Phe
    1130                1135                1140
Leu Ser Glu Lys Asn Lys Val Val Val Gly Lys Gly Glu Phe Thr
    1145                1150                1155
Lys Asp Val Gly Leu Lys Glu Met Val Phe Pro Ser Ser Arg Asn
    1160                1165                1170
Leu Phe Leu Thr Asn Leu Asp Asn Leu His Glu Asn Asn Thr His
    1175                1180                1185
Asn Gln Glu Lys Lys Ile Gln Glu Glu Ile Glu Lys Lys Glu Thr
    1190                1195                1200
Leu Ile Gln Glu Asn Val Val Leu Pro Gln Ile His Thr Val Thr
    1205                1210                1215
Gly Thr Lys Asn Phe Met Lys Asn Leu Phe Leu Leu Ser Thr Arg
    1220                1225                1230
Gln Asn Val Glu Gly Ser Tyr Asp Gly Ala Tyr Ala Pro Val Leu
    1235                1240                1245
Gln Asp Phe Arg Ser Leu Asn Asp Ser Thr Asn Arg Thr Lys Lys
    1250                1255                1260
His Thr Ala His Phe Ser Lys Lys Gly Glu Glu Glu Asn Leu Glu
    1265                1270                1275
Gly Leu Gly Asn Gln Thr Lys Gln Ile Val Glu Lys Tyr Ala Cys
    1280                1285                1290
Thr Thr Arg Ile Ser Pro Asn Thr Ser Gln Gln Asn Phe Val Thr
    1295                1300                1305
Gln Arg Ser Lys Arg Ala Leu Lys Gln Phe Arg Leu Pro Leu Glu
    1310                1315                1320
Glu Thr Glu Leu Glu Lys Arg Ile Ile Val Asp Asp Thr Ser Thr
    1325                1330                1335
Gln Trp Ser Lys Asn Met Lys His Leu Thr Pro Ser Thr Leu Thr
    1340                1345                1350
Gln Ile Asp Tyr Asn Glu Lys Glu Lys Gly Ala Ile Thr Gln Ser

-continued

```
            1355                1360                1365

Pro Leu Ser Asp Cys Leu Thr Arg Ser His Ser Ile Pro Gln Ala
            1370                1375                1380

Asn Arg Ser Pro Leu Pro Ile Ala Lys Val Ser Ser Phe Pro Ser
            1385                1390                1395

Ile Arg Pro Ile Tyr Leu Thr Arg Val Leu Phe Gln Asp Asn Ser
            1400                1405                1410

Ser His Leu Pro Ala Ala Ser Tyr Arg Lys Lys Asp Ser Gly Val
            1415                1420                1425

Gln Glu Ser Ser His Phe Leu Gln Gly Ala Lys Lys Asn Asn Leu
            1430                1435                1440

Ser Leu Ala Ile Leu Thr Leu Glu Met Thr Gly Asp Gln Arg Glu
            1445                1450                1455

Val Gly Ser Leu Gly Thr Ser Ala Thr Asn Ser Val Thr Tyr Lys
            1460                1465                1470

Lys Val Glu Asn Thr Val Leu Pro Lys Pro Asp Leu Pro Lys Thr
            1475                1480                1485

Ser Gly Lys Val Glu Leu Leu Pro Lys Val His Ile Tyr Gln Lys
            1490                1495                1500

Asp Leu Phe Pro Thr Glu Thr Ser Asn Gly Ser Pro Gly His Leu
            1505                1510                1515

Asp Leu Val Glu Gly Ser Leu Leu Gln Gly Thr Glu Gly Ala Ile
            1520                1525                1530

Lys Trp Asn Glu Ala Asn Arg Pro Gly Lys Val Pro Phe Leu Arg
            1535                1540                1545

Val Ala Thr Glu Ser Ser Ala Lys Thr Pro Ser Lys Leu Leu Asp
            1550                1555                1560

Pro Leu Ala Trp Asp Asn His Tyr Gly Thr Gln Ile Pro Lys Glu
            1565                1570                1575

Glu Trp Lys Ser Gln Glu Lys Ser Pro Glu Lys Thr Ala Phe Lys
            1580                1585                1590

Lys Lys Asp Thr Ile Leu Ser Leu Asn Ala Cys Glu Ser Asn His
            1595                1600                1605

Ala Ile Ala Ala Ile Asn Glu Gly Gln Asn Lys Pro Glu Ile Glu
            1610                1615                1620

Val Thr Trp Ala Lys Gln Gly Arg Thr Glu Arg Leu Cys Ser Gln
            1625                1630                1635

Asn Pro Pro Val Leu Lys Arg His Gln Arg Glu Ile Thr Arg Thr
            1640                1645                1650

Thr Leu Gln Ser Asp Gln Glu Glu Ile Asp Tyr Asp Asp Thr Ile
            1655                1660                1665

Ser Val Glu Met Lys Lys Glu Asp Phe Asp Ile Tyr Asp Glu Asp
            1670                1675                1680

Glu Asn Gln Ser Pro Arg Ser Phe Gln Lys Lys Thr Arg His Tyr
            1685                1690                1695

Phe Ile Ala Ala Val Glu Arg Leu Trp Asp Tyr Gly Met Ser Ser
            1700                1705                1710

Ser Pro His Val Leu Arg Asn Arg Ala Gln Ser Gly Ser Val Pro
            1715                1720                1725

Gln Phe Lys Lys Val Val Phe Gln Glu Phe Thr Asp Gly Ser Phe
            1730                1735                1740

Thr Gln Pro Leu Tyr Arg Gly Glu Leu Asn Glu His Leu Gly Leu
            1745                1750                1755
```

```
Leu Gly Pro Tyr Ile Arg Ala Glu Val Glu Asp Asn Ile Met Val
    1760            1765            1770

Thr Phe Arg Asn Gln Ala Ser Arg Pro Tyr Ser Phe Tyr Ser Ser
    1775            1780            1785

Leu Ile Ser Tyr Glu Glu Asp Gln Arg Gln Gly Ala Glu Pro Arg
    1790            1795            1800

Lys Asn Phe Val Lys Pro Asn Glu Thr Lys Thr Tyr Phe Trp Lys
    1805            1810            1815

Val Gln His His Met Ala Pro Thr Lys Asp Glu Phe Asp Cys Lys
    1820            1825            1830

Ala Trp Ala Tyr Phe Ser Asp Val Asp Leu Glu Lys Asp Val His
    1835            1840            1845

Ser Gly Leu Ile Gly Pro Leu Leu Val Cys His Thr Asn Thr Leu
    1850            1855            1860

Asn Pro Ala His Gly Arg Gln Val Thr Val Gln Glu Phe Ala Leu
    1865            1870            1875

Phe Phe Thr Ile Phe Asp Glu Thr Lys Ser Trp Tyr Phe Thr Glu
    1880            1885            1890

Asn Met Glu Arg Asn Cys Arg Ala Pro Cys Asn Ile Gln Met Glu
    1895            1900            1905

Asp Pro Thr Phe Lys Glu Asn Tyr Arg Phe His Ala Ile Asn Gly
    1910            1915            1920

Tyr Ile Met Asp Thr Leu Pro Gly Leu Val Met Ala Gln Asp Gln
    1925            1930            1935

Arg Ile Arg Trp Tyr Leu Leu Ser Met Gly Ser Asn Glu Asn Ile
    1940            1945            1950

His Ser Ile His Phe Ser Gly His Val Phe Thr Val Arg Lys Lys
    1955            1960            1965

Glu Glu Tyr Lys Met Ala Leu Tyr Asn Leu Tyr Pro Gly Val Phe
    1970            1975            1980

Glu Thr Val Glu Met Leu Pro Ser Lys Ala Gly Ile Trp Arg Val
    1985            1990            1995

Glu Cys Leu Ile Gly Glu His Leu His Ala Gly Met Ser Thr Leu
    2000            2005            2010

Phe Leu Val Tyr Ser Asn Lys Cys Gln Thr Pro Leu Gly Met Ala
    2015            2020            2025

Ser Gly His Ile Arg Asp Phe Gln Ile Thr Ala Ser Gly Gln Tyr
    2030            2035            2040

Gly Gln Trp Ala Pro Lys Leu Ala Arg Leu His Tyr Ser Gly Ser
    2045            2050            2055

Ile Asn Ala Trp Ser Thr Lys Glu Pro Phe Ser Trp Ile Lys Val
    2060            2065            2070

Asp Leu Leu Ala Pro Met Ile Ile His Gly Ile Lys Thr Gln Gly
    2075            2080            2085

Ala Arg Gln Lys Phe Ser Ser Leu Tyr Ile Ser Gln Phe Ile Ile
    2090            2095            2100

Met Tyr Ser Leu Asp Gly Lys Lys Trp Gln Thr Tyr Arg Gly Asn
    2105            2110            2115

Ser Thr Gly Thr Leu Met Val Phe Phe Gly Asn Val Asp Ser Ser
    2120            2125            2130

Gly Ile Lys His Asn Ile Phe Asn Pro Pro Ile Ile Ala Arg Tyr
    2135            2140            2145
```

```
Ile Arg Leu His Pro Thr His Tyr Ser Ile Arg Ser Thr Leu Arg
    2150            2155            2160

Met Glu Leu Met Gly Cys Asp Leu Asn Ser Cys Ser Met Pro Leu
    2165            2170            2175

Gly Met Glu Ser Lys Ala Ile Ser Asp Ala Gln Ile Thr Ala Ser
    2180            2185            2190

Ser Tyr Phe Thr Asn Met Phe Ala Thr Trp Ser Pro Ser Lys Ala
    2195            2200            2205

Arg Leu His Leu Gln Gly Arg Ser Asn Ala Trp Arg Pro Gln Val
    2210            2215            2220

Asn Asn Pro Lys Glu Trp Leu Gln Val Asp Phe Gln Lys Thr Met
    2225            2230            2235

Lys Val Thr Gly Val Thr Thr Gln Gly Val Lys Ser Leu Leu Thr
    2240            2245            2250

Ser Met Tyr Val Lys Glu Phe Leu Ile Ser Ser Ser Gln Asp Gly
    2255            2260            2265

His Gln Trp Thr Leu Phe Phe Gln Asn Gly Lys Val Lys Val Phe
    2270            2275            2280

Gln Gly Asn Gln Asp Ser Phe Thr Pro Val Val Asn Ser Leu Asp
    2285            2290            2295

Pro Pro Leu Leu Thr Arg Tyr Leu Arg Ile His Pro Gln Ser Trp
    2300            2305            2310

Val His Gln Ile Ala Leu Arg Met Glu Val Leu Gly Cys Glu Ala
    2315            2320            2325

Gln Asp Leu Tyr
    2330

<210> SEQ ID NO 2
<211> LENGTH: 21
<212> TYPE: PRT
<213> ORGANISM: artificial
<220> FEATURE:
<223> OTHER INFORMATION: Truncated B domain in FVIII. FVIII variants
      comprising this B domain linker are sometimes referred to as "N8".

<400> SEQUENCE: 2

Ser Phe Ser Gln Asn Ser Arg His Pro Ser Gln Asn Pro Pro Val Leu
1               5                   10                  15

Lys Arg His Gln Arg
            20
```